(12) United States Patent
Firminger et al.

(10) Patent No.: US 8,275,629 B2
(45) Date of Patent: *Sep. 25, 2012

(54) TEMPLATE DEVELOPMENT BASED ON REPORTED ASPECTS OF A PLURALITY OF SOURCE USERS

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 251 days.

This patent is subject to a terminal disclaimer.

(21) Appl. No.: 12/655,581

(22) Filed: Dec. 31, 2009

(65) Prior Publication Data

US 2011/0054941 A1    Mar. 3, 2011

Related U.S. Application Data

(63) Continuation-in-part of application No. 12/584,489, filed on Sep. 3, 2009, and a continuation-in-part of application No. 12/584,653, filed on Sep. 8, 2009, and a continuation-in-part of application No. 12/587,018, filed on Sep. 29, 2009, and a continuation-in-part of application No. 12/587,127, filed on Sep. 30, 2009, now Pat. No. 8,229,756, and a continuation-in-part of application No. 12/590,027, filed on Oct. 29, 2009, and a continuation-in-part of application No. 12/590,039, filed on Oct. 30, 2009, and a continuation-in-part of application No. 12/590,600, filed on Nov. 10, 2009, now Pat. No. 8,234,123, and a continuation-in-part of application No. 12/590,841, filed on Nov. 12, 2009, and a continuation-in-part of application No. 12/592,075, filed on Nov. 17, 2009, and a continuation-in-part of application No. 12/592,161, filed on Nov. 18, 2009, and a continuation-in-part of application No. 12/592,544, filed on Nov. 24, 2009, and a continuation-in-part of application No. 12/592,548, filed on Nov. 25, 2009, and a continuation-in-part of application No. 12/592,944, filed on Dec. 3, 2009, and a continuation-in-part of application No. 12/592,946, filed on Dec. 4, 2009, and a continuation-in-part of application No. 12/653,117, filed on Dec. 7, 2009, and a continuation-in-part of application No. 12/653,180, filed on Dec. 8, 2009, and a continuation-in-part of application No. 12/653,387, filed on Dec. 10, 2009, and a continuation-in-part of application No. 12/653,386, filed on Dec. 11, 2009, and a continuation-in-part of application No. 12/655,582, filed on Dec. 30, 2009, and a continuation-in-part of application No. 12/653,972, filed on Dec. 17, 2009, and a continuation-in-part of application No. 12/655,075, filed on Dec. 21, 2009, and a continuation-in-part of application No. 12/655,250, filed on Dec. 23, 2009, and a continuation-in-part of application No. 12/655,365, filed on Dec. 28, 2009.

(51) Int. Cl.
   *G06Q 10/00* (2012.01)
(52) U.S. Cl. ...................................................... 705/1.1
(58) Field of Classification Search .................. None
   See application file for complete search history.

(56) References Cited

U.S. PATENT DOCUMENTS

| | | | |
|---|---|---|---|
| 4,853,854 | A | 8/1989 | Behar et al. |
| 5,961,446 | A | 10/1999 | Beller et al. |
| 6,338,044 | B1 | 1/2002 | Cook et al. |
| 6,353,447 | B1 | 3/2002 | Truluck et al. |
| 6,842,604 | B1 | 1/2005 | Cook et al. |
| 7,587,368 | B2 | 9/2009 | Felsher |
| 7,668,735 | B2 | 2/2010 | Grace et al. |
| 7,702,685 | B2 | 4/2010 | Shrufi et al. |
| 7,860,852 | B2 | 12/2010 | Brunner et al. |
| 7,908,182 | B1 | 3/2011 | Gupta |
| 7,959,567 | B2 | 6/2011 | Stivoric et al. |
| 8,005,906 | B2 | 8/2011 | Hayashi et al. |
| 2002/0107707 | A1 | 8/2002 | Naparstek et al. |
| 2004/0015337 | A1* | 1/2004 | Thomas et al. ............... 703/11 |
| 2005/0197553 | A1 | 9/2005 | Cooper |
| 2005/0216300 | A1 | 9/2005 | Appelman et al. |
| 2006/0036619 | A1* | 2/2006 | Fuerst et al. ................ 707/100 |
| 2007/0088576 | A1 | 4/2007 | de Beus et al. |
| 2008/0091471 | A1 | 4/2008 | Michon et al. |
| 2008/0288425 | A1* | 11/2008 | Posse et al. .................. 706/12 |
| 2008/0294012 | A1* | 11/2008 | Kurtz et al. ................. 600/300 |
| 2009/0044113 | A1 | 2/2009 | Jones et al. |
| 2009/0070679 | A1 | 3/2009 | Shen et al. |
| 2009/0075242 | A1 | 3/2009 | Schwarzberg et al. |
| 2009/0076335 | A1 | 3/2009 | Schwarzberg et al. |
| 2009/0100469 | A1 | 4/2009 | Conradt et al. |
| 2009/0176526 | A1* | 7/2009 | Altman ..................... 455/556.1 |
| 2009/0258710 | A1* | 10/2009 | Quatrochi et al. ............ 463/43 |
| 2009/0271247 | A1 | 10/2009 | Karelin et al. |
| 2009/0292814 | A1 | 11/2009 | Ting et al. |
| 2009/0299990 | A1* | 12/2009 | Setlur et al. ..................... 707/5 |
| 2009/0313041 | A1* | 12/2009 | Eder ................................ 705/2 |
| 2009/0319288 | A1 | 12/2009 | Slaney et al. |
| 2009/0326981 | A1* | 12/2009 | Karkanias et al. ................ 705/3 |
| 2010/0063993 | A1* | 3/2010 | Higgins et al. ............... 709/203 |
| 2010/0114788 | A1 | 5/2010 | White et al. |
| 2010/0268830 | A1 | 10/2010 | McKee et al. |
| 2010/0281364 | A1* | 11/2010 | Sidman ........................ 715/713 |
| 2010/0293247 | A1 | 11/2010 | McKee et al. |
| 2010/0305806 | A1* | 12/2010 | Hawley .......................... 701/33 |
| 2011/0022602 | A1 | 1/2011 | Luo et al. |
| 2011/0179161 | A1 | 7/2011 | Guy et al. |
| 2011/0185020 | A1 | 7/2011 | Ramamurthy et al. |
| 2011/0252101 | A1* | 10/2011 | Davis et al. .................. 709/206 |

OTHER PUBLICATIONS

Chen, Jason; "You Can Soon Track Your Heart Rate with Your iPhone"; Gizmodo; Bearing a date of Oct. 9, 2009; p. 1: Creative Commons License: located at: http://gizmodo.com/5378340/you-can-soon-track-your-heart-rate-with-your-iphone: printed on Oct. 29, 2009.

"ErgoPR Software: Ergo Pro Computer Fatigue Software reminds you when to stretch and shows you how"; Bioexsystems.com; Bearing dates of 1995-2009: pp. 1-3; BioEx Systems Inc.; located at: http://www.bioexsystems.com/ExerciseBreak.htm; printed on Dec. 17, 2009.

"Exercise Pro Software Active Care Version 5"; Bioexsystems.com; Bearing dates of 1995-2009; pp. 1-4; BioEx Systems Inc.; located at: http://www.bioexsystems.com/ActiveCare.htm; printed on Dec. 17, 2009.

"Fitbit"; Bearing a date of 2009; pp. 1-2; Fitbit, Inc.; located at: http://www.fitbit.com; printed on Oct. 29, 2009.

"FREE Exercise Programs—Workout Routines and Weight Loss Diet Plans"; Freetrainers.com; Bearing dates of 2000-2008; pp. 1-2; located at: http://www.freetrainers.com/FT/jsp/index.jsp; printed on Sep. 2, 2009.

Guez, Tomer; "Weight Loss Software, Food Diary, Exercise Tracker, And Medical Diary: 'The Food and Exercise Diary Software Version 6.0'"; Weightlosssoftware.com; Bearing a date of Sep. 2009; pp. 1-17; TG Enterprises, Inc.; located at: http://www.weightloss-software.com/?ti=135&wn=2; printed on Dec. 17, 2009.

"Nutritionmaker Focus: Nutrition Software Motivate—Analyze—Instruct"; Bioexsystems.com; Bearing dates of 1995-2009; pp. 1-4; BioEx Systems Inc.; located at: http://www.bioexsystems.com/NutritionMakerChiro.htm; printed on Dec. 17, 2009.

"Nutrition Tracking Software is Critical for Learning about Foods and Planning Meals"; NutriCoach.net; Bearing a date of Mar. 29, 2006; 6 Total Pages; located at: http://www.nutricoach.net/diet_software.html; printed on Dec. 17, 2009.

"VHI PC—Kits Desktop Edition"; VHIKits.com; pp. 1-2; located at: http://www.vhikits.com/products/software/PCKitsDesktop.aspx; printed on Dec. 17, 2009.

Wilson, Mark; "Philips DirectLife Turns Exercise Into a Status Bar"; Gizmodo; Bearing a date of Oct. 21, 2009; pp. 1-2; Creative Commons License; located at: http://gizmodo.com/5386577/philips-directlife-turns-exercise-into-a-status-bar; printed on Oct. 29, 2009.

"Your Personalized Development Plan"; Central Michigan University; Bearing a date of 2004; p. 1; located at: http://www.chsbs.emich.edu/leader_model/dplanintro.htm; printed on Sep. 2, 2009.

Agger, Michael;"Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/655,582, Firminger et al.
U.S. Appl. No. 12/655,365, Firminger et al.
U.S. Appl. No. 12/655,250, Firminger et al.
U.S. Appl. No. 12/655,075, Firminger et al.
U.S. Appl. No. 12/653,972, Firminger et al.
U.S. Appl. No. 12/653,387, Firminger et al.
U.S. Appl. No. 12/653,386, Firminger et al.
U.S. Appl. No. 12/653,180, Firminger et al.
U.S. Appl. No. 12/653,117, Firminger et al.
U.S. Appl. No. 12/592,946, Firminger et al.
U.S. Appl. No. 12/592,944, Firminger et al.
U.S. Appl. No. 12/592,548, Firminger et al.
U.S. Appl. No. 12/592,544, Firminger et al.
U.S. Appl. No. 12/592,161, Firminger et al.
U.S. Appl. No. 12/592,075, Firminger et al.
U.S. Appl. No. 12/590,841, Firminger et al.
U.S. Appl. No. 12/590,600, Firminger et al.
U.S. Appl. No. 12/590,039, Firminger et al.
U.S. Appl. No. 12/590,027, Firminger et al.
U.S. Appl. No. 12/587,127, Firminger et al.
U.S. Appl. No. 12/587,018, Firminger et al.
U.S. Appl. No. 12/584,653, Firminger et al.
U.S. Appl. No. 12/584,489, Firminger et al.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

Gaonkar, Shravan, et al.; "Micro-Blog: Sharing and Querying Content Through Mobile Phones and Social Participation"; MobiSys '08; Jun. 17-20, 2008; pp. 174-186; ACM.

* cited by examiner

*Primary Examiner* — Jonathan Ouellette

(57) ABSTRACT

A computationally implemented method includes, but is not limited to: providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users In addition to the foregoing, other method aspects are described in the claims, drawings, and text forming a part of the present disclosure.

45 Claims, 18 Drawing Sheets

104 Template Developing Module

216 Emulatable Aspect Including Module

218 Emulatable Aspect Deriving Module

220 Commonly Reported Aspect Determining Module

222 Deviation Determining Module

224 Mean Value Determining Module

226 Average Value Determining Module

228 Compliant Determining Module

230 Plausible Emulatable Aspect Determining Module

232 Emulatable Aspect Relationship Defining Module

FIG. 2b

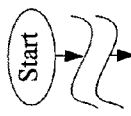
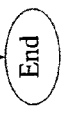

304 Developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users 532 Developing the template by including into the template one or more emulatable aspects that were derived based, at least in part, on the plurality of relevant reported aspects that are associated with the plurality of source users and that are relevant to achieving the one or more target outcomes 533 Developing the template by including into the template at least one emulatable aspect that was derived based, at least in part, on a plurality of relevant reported aspects that are each associated with different source users 542 Developing the template by including into the template at least one emulatable aspect that was derived based, at least in part, on the plurality of relevant reported aspects that are each associated with a different source user, the at least one emulatable aspect being determined to be compliant with one or more limitations associated with at least one of the one or more end users 545 Developing the template by including into the template at least one emulatable aspect that was derived based, at least in part, on the plurality of relevant reported aspects that are each associated with a different source user, the at least one emulatable aspect being determined to be compliant with one or more physical limitations associated with at least one of the one or more end users 546 Developing the template by including into the template at least one emulatable aspect that was derived based, at least in part, on the plurality of relevant reported aspects that are each associated with a different source user, the at least one emulatable aspect being determined to be compliant with one or more medical or health limitations associated with at least one of the one or more end users 547 Developing the template by including into the template at least one emulatable aspect that was derived based, at least in part, on the plurality of relevant reported aspects that are each associated with a different source user, the at least one emulatable aspect being determined to be compliant with one or more user state limitations associated with at least one of the one or more end users 548 Developing the template by including into the template at least one emulatable aspect that was derived based, at least in part, on the plurality of relevant reported aspects that are each associated with a different source user, the at least one emulatable aspect being determined to be compliant with one or more legal or regulatory limitations associated with at least one of the one or more end users

FIG. 5c

TEMPLATE DEVELOPMENT BASED ON REPORTED ASPECTS OF A PLURALITY OF SOURCE USERS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,489, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/584,653, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,018, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 29 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,127, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Sep. 2009, now U.S. Pat. No. 8,229,756.

For purposes of the USPTO extra-statutory requirements, the present application constitutes a continuation-in-part of U.S. patent application Ser. No. 12/590,027, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 29 Oct. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,039, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Oct. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,600, entitled PERSONALIZED PLAN DEVELOPMENT BASED ON IDENTIFICATION OF ONE OR MORE RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 10 Nov. 2009, now U.S. Pat. No. 8,234,123.

For purposes of the USPTO extra-statutory requirements, the present application constitutes a continuation-in-part of U.S. patent application Ser. No. 12/590,841, entitled PERSONALIZED PLAN DEVELOPMENT BASED ON IDENTIFICATION OF ONE OR MORE RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 12 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,075, entitled DEVELOPMENT OF PERSONALIZED PLANS BASED ON ACQUISITION OF RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 17 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,161, entitled DEVELOPMENT OF PERSONALIZED PLANS BASED ON ACQUISITION OF RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 18 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,544, entitled IDENTIFICATION AND PROVISION OF REPORTED ASPECTS THAT ARE RELEVANT WITH RESPECT TO ACHIEVEMENT OF TARGET OUTCOMES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 24 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,548, entitled IDENTIFICATION AND PROVISION OF REPORTED ASPECTS THAT ARE RELEVANT WITH RESPECT TO ACHIEVEMENT OF TARGET OUTCOMES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 25 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,944, entitled TEMPLATE DEVELOPMENT BASED ON SENSOR ORIGINATED REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,946, entitled TEMPLATE DEVELOPMENT BASED ON SENSOR ORIGINATED REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 4 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,117, entitled SOURCE USER BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 7 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,180, entitled SOURCE USER BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,387, entitled TARGET OUTCOME BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 10 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,386, entitled TARGET OUTCOME BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 11 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,582, entitled TEMPLATE DEVELOPMENT BASED ON REPORTED ASPECTS OF A PLURALITY OF SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,972, entitled DETECTING DEVIATION FROM COMPLIANT EXECUTION OF A TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 17 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,075, entitled DETECTING DEVIATION FROM COMPLIANT EXECUTION OF A TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 21 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,250, entitled TEMPLATE MODIFICATION BASED ON DEVIATION FROM COMPLIANT EXECUTION OF THE TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 23 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,365, entitled TEMPLATE MODIFICATION BASED ON DEVIATION FROM COMPLIANT EXECUTION OF THE TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 28 Dec. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and means for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users. In addition to the foregoing, other system aspects are described in the claims, drawings, and text forming a part of the present disclosure.

A computationally implemented system includes, but is not limited to: circuitry for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and circuitry for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users. In addition to the foregoing, other system aspects are described in the claims, drawings, and text forming a part of the present disclosure.

A computer program product including a signal-bearing medium bearing one or more instructions for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and one or more instructions for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users. In addition to the foregoing, other computer program product aspects are described in the claims, drawings, and text forming a part of the present disclosure.

A method for developing a template based, at least in part, on a plurality of relevant reported aspects associated with a plurality of source users, the method includes providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and developing, using a processor, a template designed to facilitate one or more end users to achieve the one or more target outcomes when one or more emulatable aspects included in the template are emulated, the development of the template being based, at least in part, on the providing of the plurality of relevant reported aspects associated with the plurality of source users.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2b shows another perspective of the Template Developing Module 104 of the Computing Device 10 of FIG. 1b.

FIG. 5c is a high-level logic flowchart of a process depicting alternate implementations of the template developing operation 304 of FIG. 3.

DETAILED DESCRIPTION

Figure 1A:
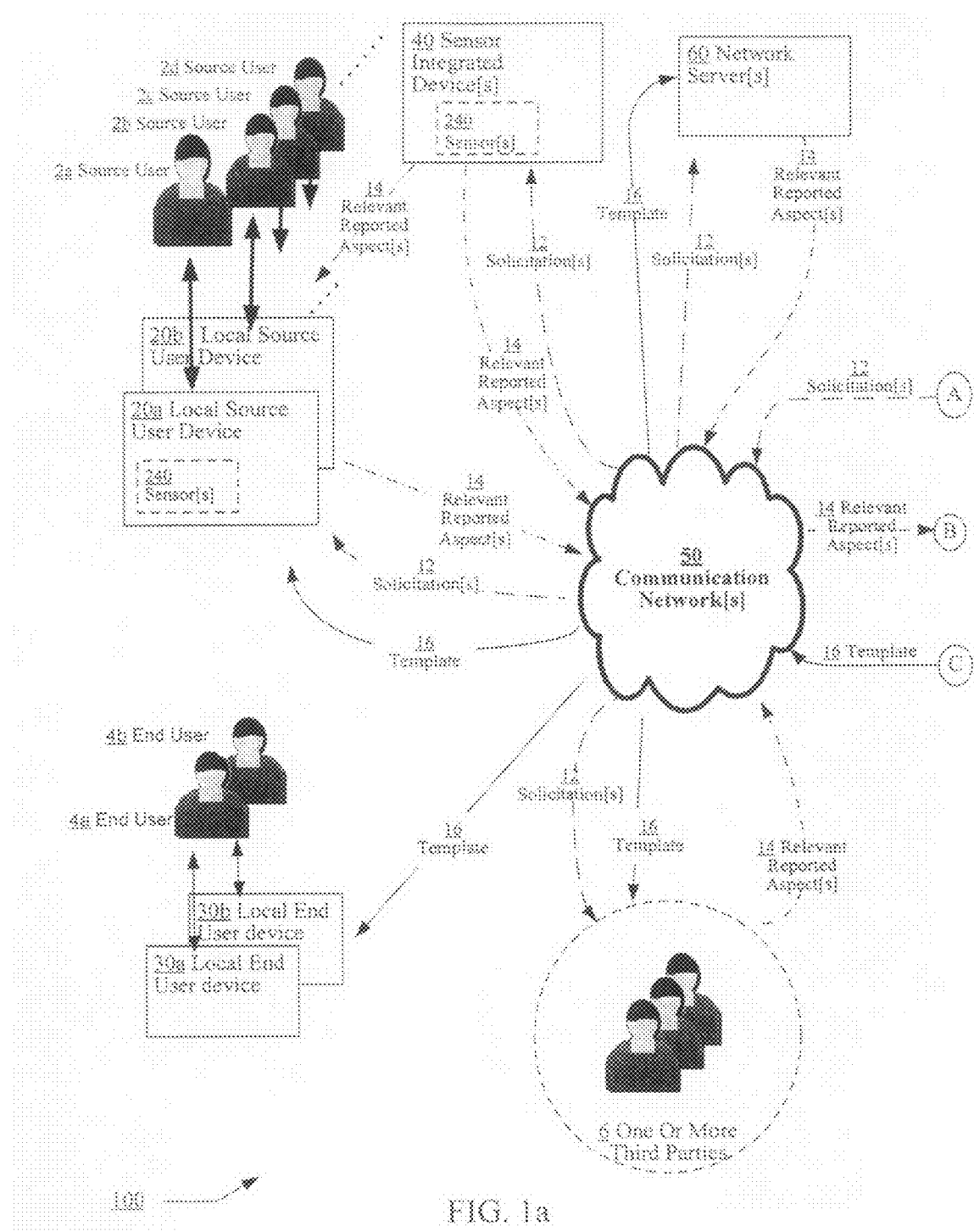
FIGS. 1a and 1b show a high-level block diagram of a Computing Device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that has enjoyed explosive popularity in the computing/communication field is to electronically record one's daily activities, behaviors, thoughts, beliefs, traits, physical or mental states, physical characteristics, and other aspects of the person's everyday life onto an open diary. One place where such open diaries are maintained is at social networking sites commonly known as "blogs" where one or more users may report or post every aspect of their daily lives. In brief, an "aspect," as will be referred to herein, may be in reference to any act, behavior, characteristic, user state or status, belief, external events, and so forth, that may be associated with a user (e.g., a person including, for example, a network user such as a blogger or a social networking user). The process of reporting or posting blog entries is commonly referred to as "blogging." A newer type of blogging that has quickly become ubiquitous in the social networking fabric is "microblogging," colloquially referred to as "twittering" or "tweeting." In microblogging, each of the microblogs that are posted are typically relatively short posts or entries, usually not more than 140 characters long.

Other types of social networking sites may also allow users to maintain open diaries and to allow users to easily update their personal information in real time. Such updates are typically made via, for example, social networking status reports otherwise known simply as "status reports." These social networking sites allow a user to report or post for others to view the latest status or other aspects related to the user.

Another recent tread in social networking is to employ one or more sensors to detect and report on a wide variety of user aspects (i.e., aspects of a user). Examples of sensors that may be used for such purposes vary widely, ranging from well-known devices that can detect and report on various physiological parameters such as heart rate or blood pressure, to sensors that can detect certain user behaviors or activities such as toilet usage. Examples of sensors that may be employed in order to monitor or detect user activities include, for example, accelerometers, pedometers, global positioning systems or GPSs, and so forth. Such devices are already, in fact, being integrated into mobile computing/communication devices such as cellular telephones and smart phones, and even into functional devices such as automobiles, exercise machines, household appliances, and so forth.

Other types of sensors are also being integrated into mobile computing/communication devices such as those that monitor environmental conditions. Examples of such sensors include, for example, those that can measure atmospheric conditions such as air quality levels. In some cases, sensors may be integrated into functional devices such as automobiles, exercise machines, household appliances, and so forth in order to detect and monitor, for example, their usage as well as, in some cases certain physical or physiological characteristics of the device operators. There are also sensors that are currently available that can even monitor bathroom or toilet usage. All the above described sensors may be configured to provide their collected data through log entries such as entries made through social networking channels (e.g., microblogs, blogs, social networking internet sites, and so forth).

Although a wealth of personal information provided through log entries (e.g., microblogs, status reports, and so forth) are now available through such social networking internet sites (or simply "social networking sites"), it is only recently has there been any effort to exploit such potentially useful data. As blogs, microblogs, and various social networking sites become increasingly popular, personal data collected through such means may be spread across multiple network locations.

One possible way to exploit such personal data is to use such data to develop templates for achieving a variety of target outcomes (e.g., goals) based on the personal data. In brief, a template may be a plan, a program, or a schedule that is designed to facilitate one or more end users to achieve one or more target outcomes when one or more events (i.e., in the following descriptions, these events will be referred to as "emulatable aspects") that may be included with the template are emulated. In other words, to use personal data of those (e.g., source users) who have already achieved desirable goals (e.g., target outcomes) to develop templates for others (e.g., end users) to emulate in order to facilitate them in achieving those goals.

Each of the one or more emulatable aspects that may be included in a template may be based on and correspond to one or more reported aspects of one or more source users that may have been reported through, for example, social networking channels (e.g., microblogs, social networking sites, and so forth). An "aspect," in brief may be any behavior, act, mental state, physical state, and so forth that may be associated with a source user. A "reported aspect" is any aspect associated with a source user that may have been reported via, for example, one or more social networking channels or by other means.

There are at least two types of templates that could be developed from personal data obtained through, for example, social networking channels. One type of templates that can be developed is generic templates that may be designed to be used generically by any random user in order to achieve one or more target outcomes. The second type of templates, which may be referred to as personalized templates or personalized plans, include those templates that have been personalized for use by a particular end user or users (e.g., a modified version of a generic template that has been modified in order to accommodate the end user's limitations and/or preferences). For purposes of this description, references to a "template" in the following will be in reference to either the first or the second type of templates.

In various embodiments, methods, systems, circuitry, and computer program products are provided that are designed to develop a template that is designed to facilitate one or more end users to achieve one or more target outcomes when one or more emulatable aspects included in the template are emulated, the development of the template being based, at least in part, on relevant reported aspects of a plurality of source users, the relevant reported aspects being relevant to achieving the one or more target outcomes. In some embodiments, the relevant reported aspects of the plurality of source users may have been originally reported via log entries such as microblog entries and status reports. More generally, the methods, systems, circuitry, and computer program products to be provided are designed to facilitate the development of a template based on reported aspects of multiple source users. These methods, systems, circuitry, and computer program products being very dynamic and are able to facilitate in the development of almost any type of template to achieve almost any type of target outcomes.

As previously described a "template" may be any type of plan, program, or schedule that is designed to facilitate achievement of one or more target outcomes when one or more emulatable aspects included in the template are emulated. Each of the one or more emulatable aspects that may be included in the template may have been developed based on a plurality of relevant reported aspects that are each associated with a different source user. In various embodiments, each of the associated source users may or may not have originally reported the associated relevant reported aspect. That is, a reported aspect (e.g., a relevant or non-relevant reported aspect) of a source user may be reported by any one of a number of different sources including, for example, by the source user (e.g., a microblogger or a social networking user) who is the basis for the reported aspect, by a sensor, or by a third party (e.g., such as another source user).

As briefly described earlier, a template may comprise of one or more emulatable aspects that may be based on reported aspects of, for example, one or more source users. Note that the word "emulatable" as will be repeatedly used herein has no significant meaning other than to be used in the following description to merely distinguish those aspects (emulatable aspects) that are indicated in a template from other types of aspects (e.g., reported aspects of source users). In accordance with various embodiments, a template may be developed for achieving almost any type of desired outcome (e.g., target outcome) so long as the appropriate data, such as log entry data of source users who have achieved the desired outcome, are available. Examples of the types of templates that could be developed based on log entry data include, for example, those that are designed to facilitate achievement of medical or health related outcomes, those that are designed to facilitate achievement of athletic or gaming outcomes, those that are designed to facilitate achievement of particular user states such as mental or social states, those that are designed to facilitate achievement of intellectual or academic outcomes, and so forth.

In some cases, a template may merely indicate or be a collection of one or more emulatable aspects that end users may emulate in order to achieve one or more target outcomes. In other instances, however, a template may indicate a plurality of emulatable aspects and may define their relationships (e.g., temporal or specific time relationship) with respect to each other. Such a template will be very similar to a schedule or program that indicates when each of the emulatable aspects included in the template should be emulated by end users with respect to the other emulatable aspects included in the template. For example, if a template is designed to facilitate end users to shed a certain amount of body weight, it may include a schedule of when and what activities (e.g., go jogging for 30 minutes on day 1, go swimming for 40 minutes on day 2, and so forth) end users may need to execute in order to achieve the weight loss. Similarly, if the template is designed to, for example, facilitate end users to achieve a high score for the scholastic aptitude test (SAT), the template may be a schedule of when and what activities (e.g., read a particular book on day 1, work on math problems from a particular math book on day 2, and so forth) end users may need to execute in order to achieve the high test score for the SAT.

In some instances a template may include one or more emulatable intermediate outcomes that are related to the one or more target outcomes associated with the template. For example, in the above weight loss example, the template may indicate the amount of weight loss end users should have achieved (e.g., in order to achieve the target outcome) after emulating, for example, one week, two weeks, or a month of emulatable aspects indicated by the template.

In still other cases, a template may merely be a collection of emulatable aspects that does not define the relationships between the emulatable aspects. For example, a template designed to facilitate an end user to achieve relaxed state of mind may indicate two unlinked emulatable aspects, "get 8 hours of sleep each night," and "avoid caffeine beverages." Such a template would not necessarily have any indication of relationship between the two emulatable aspects indicated by the template. It should be noted here that an emulatable aspect that may be included into a template may not only be an act or a behavior, but may be a physiological characteristic, a mental state, or any other aspect that may be emulated. For example, a template that is designed to facilitate reducing backaches may include as one of its aspects, a requirement to keep blood pressure below a certain level, which is a physiological state. An emulatable aspect may even be an external event, such as environmental conditions, that an end user may have some control over.

In some embodiments, a template may include or be linked to other information other than emulatable aspects. For example, in some instances, a template may include or be associated with a particular source user and/or with a particular target outcome. Other information may also be included with or be associated with a template as will be further described herein.

In order to facilitate understanding of the various concepts to be described herein, an introduction to the meaning of certain words and phrases to be used in the following discussion will now be provided. As described earlier, an "aspect" may be any occurrence of any behavior, act, belief, characteristic, user state or status, external event, or any other facet associated with a source user or a group of source users. A "source user" may be any person, such as a microblogger or a social networking user, who may be the basis for one or more reported aspects. Note that a source user may not necessarily have to be the source for the one or more reported aspects that are related to the source user since reported aspects that are associated with a particular source user may be provided by other source users or by sensors.

A "reported aspect" may be any aspect associated with or related to a source user or an end user that has been reported by, for example, the source user, the end user, one or more sensors, or one or more third parties (e.g., other source users or end users). In some instances, such a reported aspect may be reported in the form of a log entry such as a microblog entry, a status report, or a journal entry.

A "target outcome" may be any type of desirable goal or result that may be sought by, for example, end users. Examples of target outcomes include, for example, health-related outcomes such as weight loss or improved cardiovascular conditioning, athletic outcomes such as developing a particular athletic skill including being able to pitch a curve ball or achieving a particular golf handicap, physiological outcomes such as reduced blood pressure or blood glucose levels, social outcomes such as obtaining membership into an elite social club or attaining a particular social status, mental state outcomes such as achieving certain level of calmness or happiness, interpersonal or relational outcomes such as having lots of friends or developing skill to make friends, employment outcomes such as being promoted or developing certain work skills, academic or intellectual outcomes, and so forth.

An "end user" may be any person, for example, who executes a template in order to achieve one or more target outcomes. As briefly described above, a "source user" may be any person who may be the basis for one or more reported aspects. Note that although in most cases, a source user will be an actual (real) person who may be the basis for one or more reported aspects, in other cases, however, a source user may be a fictional person such as a composite of multiple "actual" source users. For example, reported aspects indicating actual aspects of a plurality of actual source users may be compiled and processed (e.g., normalized or averaged out) in order to create a fictional source user.

Figure 1B:
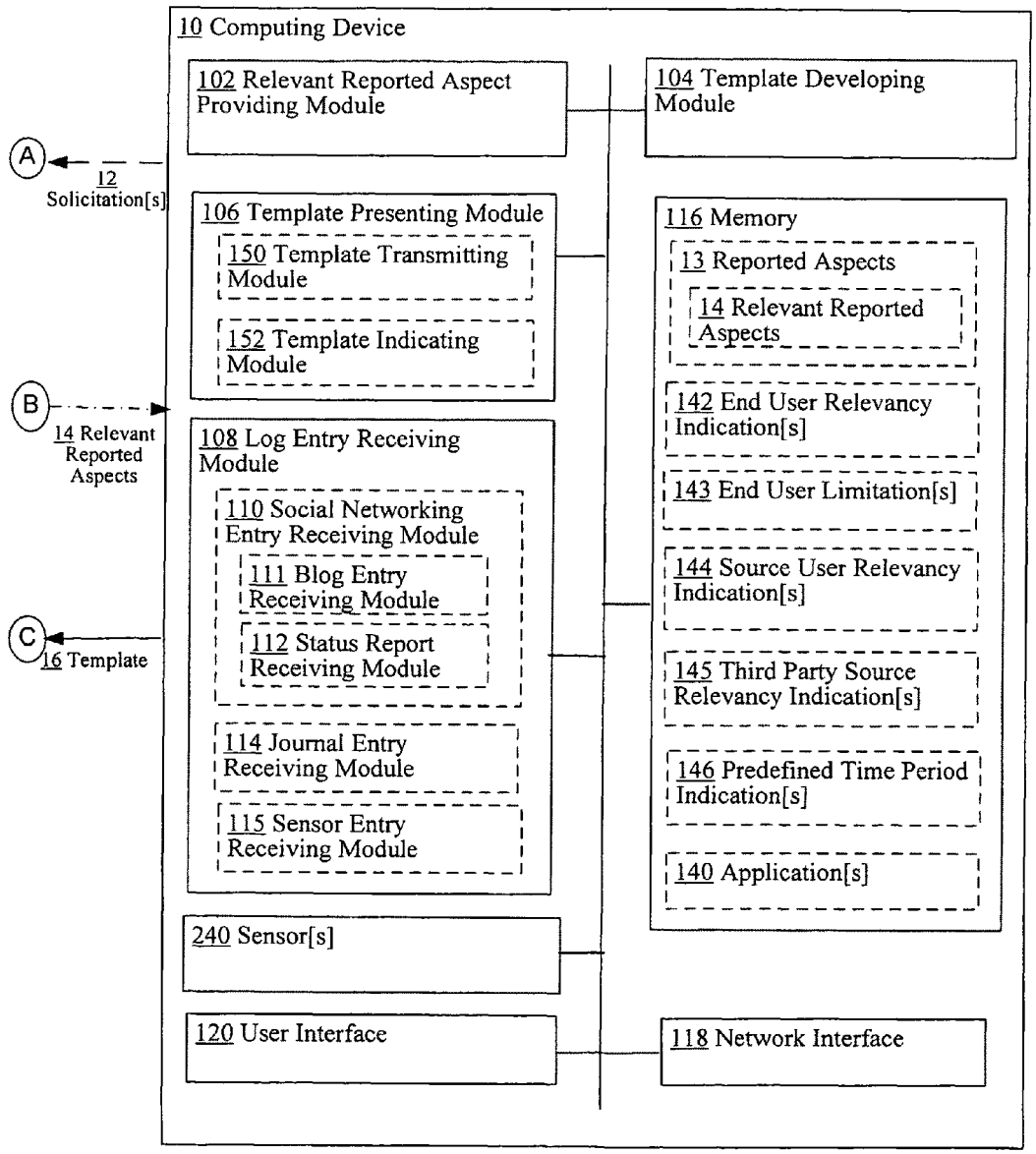

Turning now to FIGS. 1a, and 1b illustrating an example environment in which the methods, systems, circuitry, and computer program products in accordance with various embodiments may be implemented by a computing device 10. In particular, the methods, systems, circuitry, and computer program products may be implemented at any network device including at a peer-to-peer network component device. In some embodiments, the computing device 10 may be a server such as one of the one or more network servers 60 illustrated in FIG. 1a. Alternatively, the computing device 10 may be a source user device such as one of the local source user devices 20* illustrated in FIG. 1a. In still other embodiments, the computing device 10 may be an end user device such as one of the local end user devices 30* illustrated in FIG. 1a. Note that in the following, "*" represents a wildcard. Thus, references in the following description to, for example, "a source user 2*" may be in reference to a source user 2a, a source user 2b, a source user 2c, and so forth, or a combination thereof.

Note further that for ease of understanding and explanation, the computing device 10 of the exemplary environment 100 of FIGS. 1a and 1b in the following discussion will be generally described operating as a server (e.g., server embodiment) rather than as an end user device or as a source user device. Further, although the following discussion related to the exemplary environment 100 of FIGS. 1a and 1b assumes that the computing device 10 is a server, the following discussion will, for the most part, be applicable even if the computing device 10 were operating as an end user device (e.g., local end user device 30*) or as a source user device (e.g., local source user device 20*) with certain obvious exceptions (e.g., if the computing device 10 is an end user device or a source user device rather than a server, the computing device 10 may communicate with an end user 4* or a source user 2* directly through a user interface 120 rather than indirectly through one or more communication networks 50 as may be the case when the computing device 10 is a server). In some embodiments, the computing device 10 may operate via a web 1.0 or web 2.0 construct.

Referring back to FIGS. 1a and 1b, and as previously indicated, the computing device 10 may be a network device such as a server (e.g., a network server 60) that is designed to communicate with other network devices. For example, the computing device 10 may communicate with one or more source users 2* (e.g., source user 2a, source user 2b, source user 2c, source user 2d, and so forth) through one or more local source user devices 20* (e.g., local source user device 20a, local source user device 20b, and so forth), with a plurality of end users 4* (e.g., end user 4a, end user 4b, and so forth) through a plurality of local end user devices 30* (e.g., local end user device 30a, local end user device 30b, and so forth), with one or more sensor integrated devices 40 (e.g., a transportation vehicle such as a car, an exercise machine, or any other type of functional device that may have an integrated sensor designed to sense, for example, their usage or some aspect of the device operator), with one or more network servers 60, and/or with one or more third parties 6 (e.g., one or more content providers, one or more network service providers, and/or one or more potential future end users 4*) via one or more communication networks 50. In some implementations, the one or more communication networks 50 may include one or more wireless networks and/or one or more wired networks including, for example, at least one of a local area network (LAN), a wireless local area network (WLAN), personal area network (PAN), Worldwide Interoperability for Microwave Access (WiMAX), public switched telephone network (PTSN), general packet radio service (GPRS), cellular networks, and/or other types of wireless and/or wired networks.

In some implementations, the computing device 10 may be designed to develop at least one template 16 that is designed to facilitate one or more end users 4* to achieve one or more target outcomes when one or more emulatable aspects included in the template 16 are emulated. The development of the template 16 may be based on a plurality of relevant reported aspects 14 associated with a plurality of source users 2* that are determined to be relevant to achieving the one or more target outcomes. In some cases, the relevant reported aspects 14 may have been originally reported via log entries such as microblog entries and/or status reports. A log entry may be any entry that indicates any aspect of, for example, a source user 2* that may be entered continuously, regularly, semi-regularly, randomly, or on a one-time basis.

In some cases, the computing device 10 may have previously received a number of reported aspects 13 that include the relevant reported aspects 14 (e.g., the reported aspects 13 may include both relevant reported aspects 14 and non-relevant reported aspects). After receiving the reported aspects 13 including the relevant reported aspects 14, the reported aspects 13 including the relevant reported aspects 14 may be stored in a memory 116. In various embodiments, the reported aspects 13 as well as the relevant reported aspects 14 may be obtained from a variety of sources including for example, one or more network servers 60, local source user devices 20*, one or more sensor integrated devices 40, and/or one or more third parties 6.

Alternatively, the plurality of relevant reported aspects 14 may be selectively acquired by the computing device 10 as a result of the computing device 10 transmitting one or more solicitations 12 that solicits for the relevant reported aspects 14. Such solicitations 12 may be sent to a variety of network devices including, for example, to one or more network servers 60, one or more sensor integrated devices 40, local source user devices 20*, and so forth. Note that in embodiments where the computing device 10 receives a plurality of reported aspects 13 including a plurality of relevant reported aspects 14, the computing device 10 may, after receiving the plurality of reported aspects 13, store the reported aspects 13 (as well as the relevant reported aspects 14 in a memory 116). After acquiring the relevant reported aspects 14, a template 16 may be developed based, at least in part, on the identification of the relevant reported aspects 14 (associated with multiple source users 2*) from a plurality of reported aspects 13. In some cases, the template 16 may be developed by including into the template 16 one or more emulatable aspects that are each developed based on relevant reported aspects 14 of multiple source users 2*.

In embodiments where the template 16 includes a plurality of emulatable aspects the development of the template 16 may further include defining in the template 16 the relationships (e.g., temporal or specific time relationships) between the plurality of emulatable aspects that may be included in the template 16. Such relationships may also be based, at least in part, on the plurality of relevant reported aspects 14 of the plurality of source users 2*.

After developing the template 16, the template 16 may be presented to at least one end user 4*, to one or more network servers 60, to one or more third parties 6, or to one or more source users 2* via one or more communication networks 50. In embodiments in which the computing device 10 is a local client device such as local end user device 30* or a local source user device 20*, the template 16 may be presented via a user interface 120.

In various embodiments, the computing device 10 may be a server (e.g., one of the one or more network servers 60) that may be located at a single network site, located across multiple network sites, or may be a conglomeration of servers located at multiple network sites. In embodiments in which the computing device 10 is a source user device (e.g., local source user device 20*) or an end user device (e.g., local end user device 30*) rather than a network server 60, the computing device 10 may be any one of a wide range of mobile or stationary computing/communication devices including, for example, a laptop, a desktop, a workstation, a cellular telephone, a personal digital assistant (PDA), a Smartphone, a web tablet such as a Netbook, and so forth.

Referring back to the exemplary environment 100 of FIGS. 1a and 1b, in various embodiments the one or more sensor integrated devices 40 of the exemplary environment 100 of FIGS. 1a and 1b may directly communicate with the one or more communication networks 50. Alternatively, the one or more sensor integrated devices 40 may indirectly communicate with the one or more communication networks 50 via the one or more local source user devices 20* (e.g., via, for example, a personal area network or PAN). In various alternative embodiments, a sensor integrated device 40 may be a variety of functional devices that may comprise of one or more sensors 240 and that may be operated or used by a source user 2*. Examples of such devices include, for example, a transportation vehicle (e.g., automobile, a motorcycle, a boat, a plane, and so forth), an exercise machine (e.g., a treadmill), a household appliance (e.g., television set), and so forth.

As will be further described herein, the one or more sensors 240, which may also be included in the local source user devices 20*, the one or more local end user devices 30*, and/or the computing device 10, may include any type of sensors 240 that can sense one or more aspects of a source user 2* or, in some cases, an end user 4*. Examples of such sensors 240 include, for example, sensing devices that can sense various physical characteristics of a source user 2* or an end user 4* (e.g., heart rate sensor or blood pressure sensor), sensing devices that can sense activities of a source user 2* or an end user 4* (e.g., a pedometer, an accelerometer, and so forth), sensing devices that can sense environment conditions (e.g., air quality sensors), sensing devices that can sense the location of a source user 2* or an end user 4* (e.g., global positioning system or GPS), sensing devices that can provide physiological data that may be processed in order to determine inferred mental states of source users 2* or end users 4*, and so forth.

Each of the one or more local source user devices 20* and the local end user devices 30* (as well as the computing device 10 in embodiments in which the computing device 10 is an end user device or a source user device) may be any one of a variety of computing/communication devices including, for example, a cellular phone, a personal digital assistant (PDA), a laptop, a desktop, or other types of computing/communication devices. In some embodiments, the one or more local source user devices 20* and/or the local end user devices 30* (as well as the computing device 10 in some embodiments) may be a handheld device such as a cellular telephone, a Smartphone, a Mobile Internet Device (MID), an Ultra Mobile Personal Computer (UMPC), a convergent device such as a personal digital assistant (PDA), and so forth. Alternatively, such local client devices (e.g., local source user device 20* and/or local end user devices 30*) may be a laptop, a desktop, a workstation, a web tablet such as a Netbook, or other types of devices that may not be a handheld device in various alternative implementations.

Figure 2A:
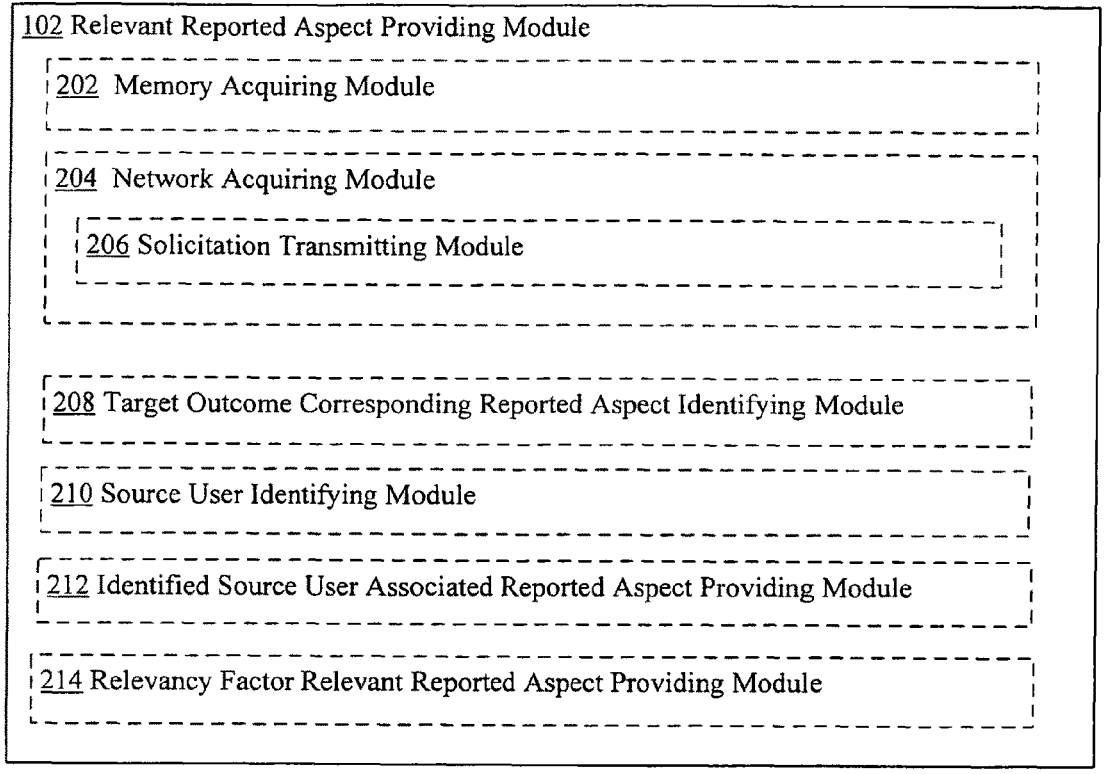
FIG. 2a shows another perspective of the Relevant Reported Aspect Providing module 102 of the Computing Device 10 of FIG. 1b.

The computing device 10 as illustrated in FIG. 1b may include one or more modules, sub-modules, and various other components. As shown, the computing device 10 may include at least a relevant reported aspect providing module 102 (which may further include one or more sub-modules as illustrated in FIG. 2a) and a template developing module 104 (which may also include one or more sub-modules as illustrated in FIG. 2b). The relevant reported aspect providing module 102 may be particularly configured to, among other things, provide a plurality of relevant reported aspects 14 associated with a plurality of source users 2* that are relevant to achieving one or more target outcomes, the providing of the plurality of relevant reported aspects 14 being based, at least in part, on relevancy of the plurality of relevant reported aspects 14 with respect to the one or more target outcomes. In contrast, the template developing module 104 may be particularly configured to, among other things, develop a template 16 designed to facilitate one or more end users 4* to achieve the one or more target outcomes when one or more emulatable aspects included in the template 16 are emulated, the development of the template 16 being based, at least in part, on the providing of the plurality of relevant reported aspects 14 associated with the plurality of source users 2*.

In various implementations, the computing device 10 may further include a template presenting module 106 and a memory 116. The template presenting module 106 may be particularly configured to present the template 16 to, for example, one or more end users 4*, to one or more network servers 60, or to one or more third parties 6. In some implementations, the template presenting module 106 may further include a template transmitting module 150 (e.g., configured to transmit, via the one or more communication networks 50, the template 16) and/or a template indicating module 152 (e.g., configured to indicate, via the user interface 120, the template 16).

The memory 116, in various implementations, may store a plurality of reported aspects 13 that are associated with the plurality of source users 2*. Among the plurality of reported aspects 13 stored in memory 116 may be a plurality of relevant reported aspects 14 that may be determined to be relevant to achieving the one or more target outcomes of the template 16 that is developed by the template developing module 104. Other types of data may also be stored in the memory 116 in various alternative implementations. For example, in various implementations, the memory 116 may store one or more of end user relevancy indications 142 (e.g., one or more indications that indicate the types of reported or emulatable aspects that one or more end users 4* have an interest in or believes are relevant to achieving one or more target outcomes), one or more end user limitations 143 (e.g., limitations such as contextual limitations, physical limitations, personal limitations, and so forth, associated with one or more end users 4* that prevent one or more emulatable aspects of the template 16 from being emulated by the one or more end users 4*), and/or one or more source user relevancy indications 144 (e.g., one or more indications provided by one or more source users 2* that indicate at least which types of reported aspects 13 are relevant to achieving one or more target outcomes).

In some cases, the memory 116 may also include, for example, one or more third party source relevancy indications 145 (e.g., one or more indications provided by one or more third party sources such as one or more third parties 6 that indicate at least which types of reported aspects 13 are relevant to achieving one or more target outcomes), and/or one or more predefined time period indications 146 (e.g., one or more indications that indicate at least one time period such as a time increment or window that may be used to determine whether, for example, a reported aspect 13 is relevant for achieving at least one target outcome only if the reported aspect 13 indicates an aspect that occurred within the at least one time period from an occurrence of the target outcome as successfully achieved by, for example, a source user 2*).

In some implementations, the memory 116 may store one or more applications 140 (e.g., a text messaging application, an instant messaging application, an email application, a social networking application, a voice recognition system, a Web 1.0 application, and/or Web 2.0 application to facilitate in communicating via, for example, the World Wide Web). The memory 116 may comprise of one or more of a mass storage device, a read-only memory (ROM), a programmable read-only memory (PROM), an erasable programmable read-only memory (EPROM), a cache memory such as random access memory (RAM), a flash memory, a synchronous random access memory (SRAM), a dynamic random access memory (DRAM), and/or other types of memory devices.

The computing device 10 may also include, in various implementations, a network interface 118 (e.g., a network interface card or NIC), a user interface 120 (e.g., a display monitor, a touchscreen, a microphone, a speaker, a mouse, and so forth), and/or one or more sensors 240 that are designed to measure or sense one or more user aspects. Examples of sensors 240 include, for example, devices that are designed to sense user activities such as pedometers and accelerometers, devices that are designed to sense physiological characteristics such as heart rate monitors or blood glucose monitors, devices that are designed to sense environmental conditions such as devices for measuring air quality, devices that are designed to detect user location such as GPS, and so forth. In some cases, the presence or absence of some of these modules and components of computing device 10 may depend on, for example, whether the computing device 10 is a server, an end user device, or a source user device. For example, if the computing device 10 is a server, then the computing device 10 may not include a user interface 120.

In various implementations, the computing device 10 may include a log entry receiving module 108 that is particularly configured to receive log entries associated with a plurality of source users 2*. In some implementations, the log entry receiving module 108 may further include one or more additional sub-modules. For example, in some instances, the log entry receiving module 108 may include a social networking entry receiving module 110 that is configured to receive social networking entries (e.g., log entries provided through social networking channels such as social networking sites). The social networking entry receiving module 110 may further include a blog entry receiving module 111 (e.g., configured to receive blog entries) and/or a status report receiving module 112 (e.g., configured to receive social networking status reports). In the same or different implementations, the log entry receiving module 108 may further include a journal entry receiving module 114 (e.g., configured to receive journal or diary entries) and/or sensor entry receiving module 115 (e.g., configured to receive log entries provided by sensors 240).

FIG. 2a illustrates particular implementations of the relevant reported aspect providing module 102 of FIG. 1b. The relevant reported aspect providing module 102 in various implementations may include, among other things, a memory acquiring module 202 that is configured to, among other things, acquire one or more of the plurality of relevant reported aspects 14 that are relevant to achieving one or more target outcomes from a memory 116 and/or a network acquiring module 204 that is configured to acquire one or more of the plurality of relevant reported aspects 14 via one or more communication networks 50 and that may include a solicitation transmitting module 206 that is configured to transmit one or more solicitations 12 for the one or more relevant reported aspects 14 via the one or more communication networks 50.

In the same or different implementations, the relevant reported aspect providing module 102 may include a "target outcome corresponding reported aspect" identifying module 208, a source user identifying module 210, an identified source user associated reported aspect providing module 212, and/or a "relevancy factor relevant reported aspect" providing module 214. A more detailed discussion regarding these sub-modules of the relevant reported aspect providing module 102 will be provided with respect to the processes and operations to be described herein.

FIG. 2b illustrates particular implementations of the template developing module 104 of the computing device 10 of FIG. 1b. In various implementations, the template developing module 104 may include at least an emulatable aspect including module 216 that may be particularly configured to include into a template 16 one or more emulatable aspects. Each of the one or more emulatable aspects to be included in the template 16 by the emulatable aspect including module 216 may have been developed based on a plurality of relevant reported aspects 14 of a plurality of source users 2*. The emulatable aspect including module 216 may further include an emulatable aspect deriving module 218 that may be particularly configured to derive the one or more emulatable aspects to be included in the template 16. The emulatable aspect deriving module 218 may, in turn, further include a commonly reported aspect determining module 220, a deviation determining module 222 (which may further include a mean value determining module 224 and/or an average value determining module 226), a compliant determining module 228, and/or a plausible emulatable aspect determining module 230. These modules and sub-modules of the template developing module 104 will be discussed in greater detail below with respect to the processes and operation to be described herein.

In some implementations, the template developing module 104 may further include an emulatable aspect relationship defining module 232 that is configured to define one or more relationships (e.g., temporal or specific time relationships) between emulatable aspects in a template 16 when the template 16 includes a plurality of emulatable aspects. Such relationships may be based, at least in part, on the relevant reported aspects 14 provided by the relevant reported aspect providing module 102. In some cases, such relationships may also be provided by using techniques similar to the techniques that will be described herein that may be used in order to derive the emulatable aspects to be included in the template 16. In other cases, such relationships may be determined by determining trends that may be detected with respect to how relevant reported aspects 14 were executed by the source users 2*. In still other cases, more sophisticated analysis may be performed in order to determine the relationships between the emulatable aspects that may be included in a template 16.

Referring back to the computing device 10 of FIG. 1b, the various modules (e.g., the relevant reported aspect providing module 102, the template developing module 104, and so forth) along with their sub-modules included in the computing device 10 may be implemented using hardware, software, firmware, or any combination thereof. For example, in some implementations, the relevant reported aspect providing module 102 and/or the template developing module 104 may be implemented with a processor 802 (e.g., microprocessor, controller, and so forth) executing computer readable instructions 804 (e.g., computer program product) stored in a storage medium 806 (e.g., volatile or non-volatile memory) such as a signal-bearing medium as depicted in the computing device 10 of FIG. 8. Alternatively, hardware such as application specific integrated circuit (ASIC) may be employed in order to implement such modules in some alternative implementations.

Figure 3:
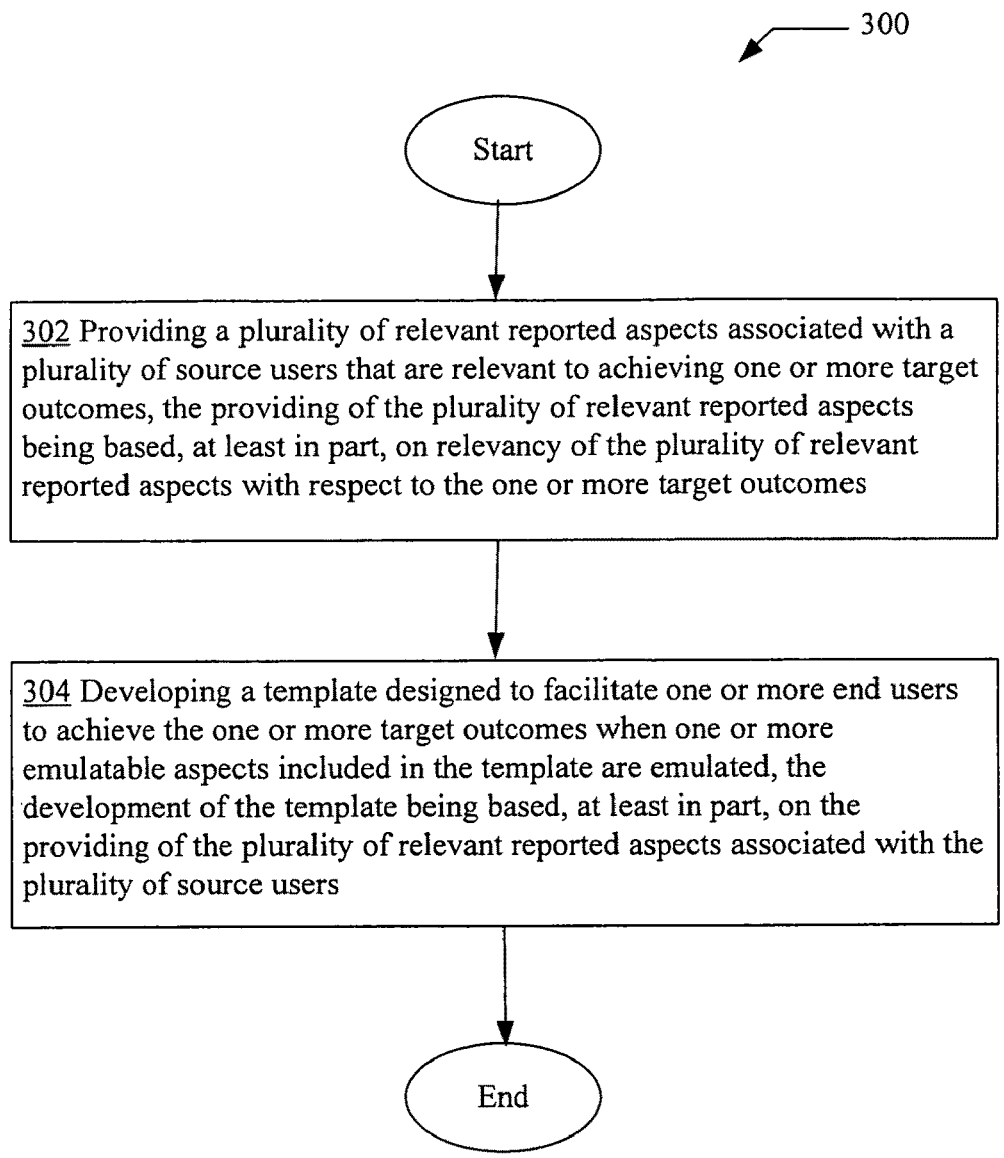
FIG. 3 is a high-level logic flowchart of a process.

A more detailed description of the computing device 10 of FIG. 1b and its components will now be provided with respect to the processes and operations to be described herein. FIG. 3 illustrates an operational flow 300 representing example operations directed to, among other things, development of a template 16 that is designed to facilitate one or more end users 4* to achieve the one or more target outcomes when one or more emulatable aspects included in the template 16 are emulated, the development of the template 16 being based, at least in part, on relevant reported aspects 14 of a plurality of source users 2* that are relevant to achieving the one or more target outcomes.

In FIG. 3 and in the following figures that include various examples of operational flows, discussions and explanations of the operational flows will be provided with respect to the exemplary environment 100 described above as illustrated in FIGS. 1a and 1b, and/or with respect to other examples (e.g., as provided in FIGS. 2a and 2b) and contexts. However, it should be understood that the operational flows may be executed in a number of other environments and contexts, and/or in modified versions of FIGS. 1a, 1b, 2a, and 2b. Also, although the various operational flows are presented in the sequence(s) illustrated, it should be understood that the various operations may be performed in other orders other than those which are illustrated, or may be performed concurrently.

Further, in FIG. 3 and in the figures to follow thereafter, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a relevant reported aspect providing operation 302 for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes. For instance, and as an illustration, the relevant reported aspect providing module 102 of the computing device 10 of FIG. 1b providing (e.g., acquiring, retrieving, identifying, finding, locating, accessing, and so forth) a plurality of relevant reported aspects 14 associated with a plurality of source users 2* that are relevant to achieving one or more target outcomes (e.g., health or medical outcomes, athletic or fitness outcomes, user state outcomes such as subjective mental state outcomes, spiritual outcomes, and so forth), the providing of the plurality of relevant reported aspects 14 being based, at least in part, on relevancy of the plurality of relevant reported aspects 14 with respect to the one or more target outcomes.

In addition to the relevant reported aspect providing operation 302, operational flow 300 may also include a template developing operation 304 for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users. For instance, the template developing module 104 of the computing device 10 developing a template 16 that is designed to facilitate one or more end users 4* to achieve the one or more target outcomes when one or more emulatable aspects included in the template 16 are emulated, the development of the template 16 being based, at least in part, on the providing of the plurality of relevant reported aspects 14 associated with the plurality of source users 2*. Note that in various implementations, the relevant reported aspect providing operation 302 and the template developing operation 304 of FIG. 3 may be implemented in a variety of different ways.

Figure 4A:
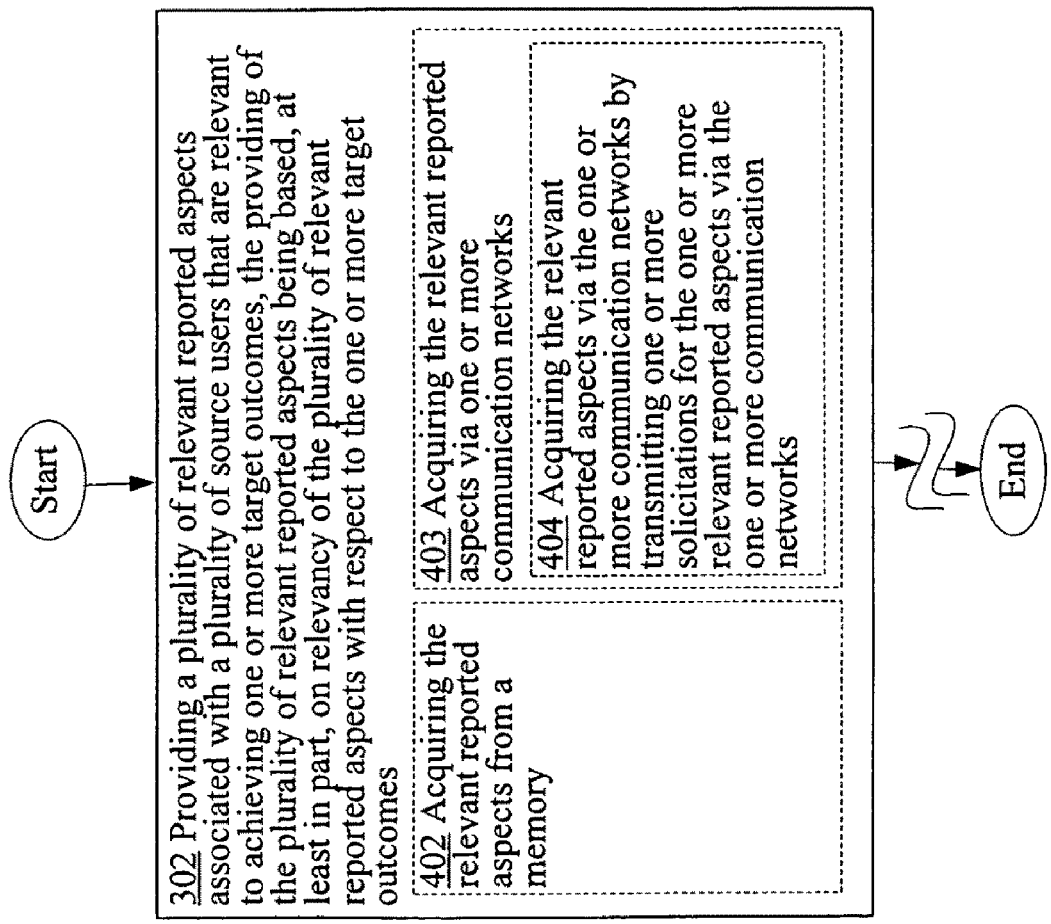
FIG. 4a is a high-level logic flowchart of a process depicting alternate implementations of the relevant reported aspect providing operation 302 of FIG. 3.

For example, FIGS. 4a, 4b, 4c, 4d, and 4e illustrate various ways that the relevant reported aspect providing operation 302 of FIG. 3 may be executed in various alternative implementations. For instance, the relevant reported aspects 14 provided through operation 302 may be provided from various sources in various alternative implementations. In some implementations, for example, the relevant reported aspect providing operation 302 may include an operation 402 for acquiring the relevant reported aspects from a memory as depicted in FIG. 4a. For instance, the memory acquiring module 202 (see FIG. 2a) of the computing device 10 acquiring (e.g., locating, finding, retrieving, identifying, and so forth) the relevant reported aspects 14 from a memory 116 (e.g., volatile or non-volatile memory including, for example, cache memory).

In some implementations, the relevant reported aspect providing operation 302 may include an operation 403 for acquiring the relevant reported aspects via one or more communication networks as depicted in FIG. 4a. For instance, the network acquiring module 204 (see FIG. 2a) of the computing device 10 acquiring (e.g., soliciting, querying, retrieving, receiving, and so forth) the relevant reported aspects 14 via one or more communication networks 50 (e.g., a wireless network and/or a wired network).

In some cases, operation 403 may, in turn, include an operation 404 for acquiring the relevant reported aspects via the one or more communication networks by transmitting one or more solicitations for the one or more relevant reported aspects via the one or more communication networks as depicted in FIG. 4a. For instance, the network acquiring module 204 of the computing device 10 acquiring the relevant reported aspects 14 via the one or more communication networks 50 by having the solicitation transmitting module 206 (see FIG. 2a) transmitting one or more solicitations 12 (e.g., requests, queries, and so forth) for the one or more relevant reported aspects 14 via the one or more communication networks 50.

Figure 4B:
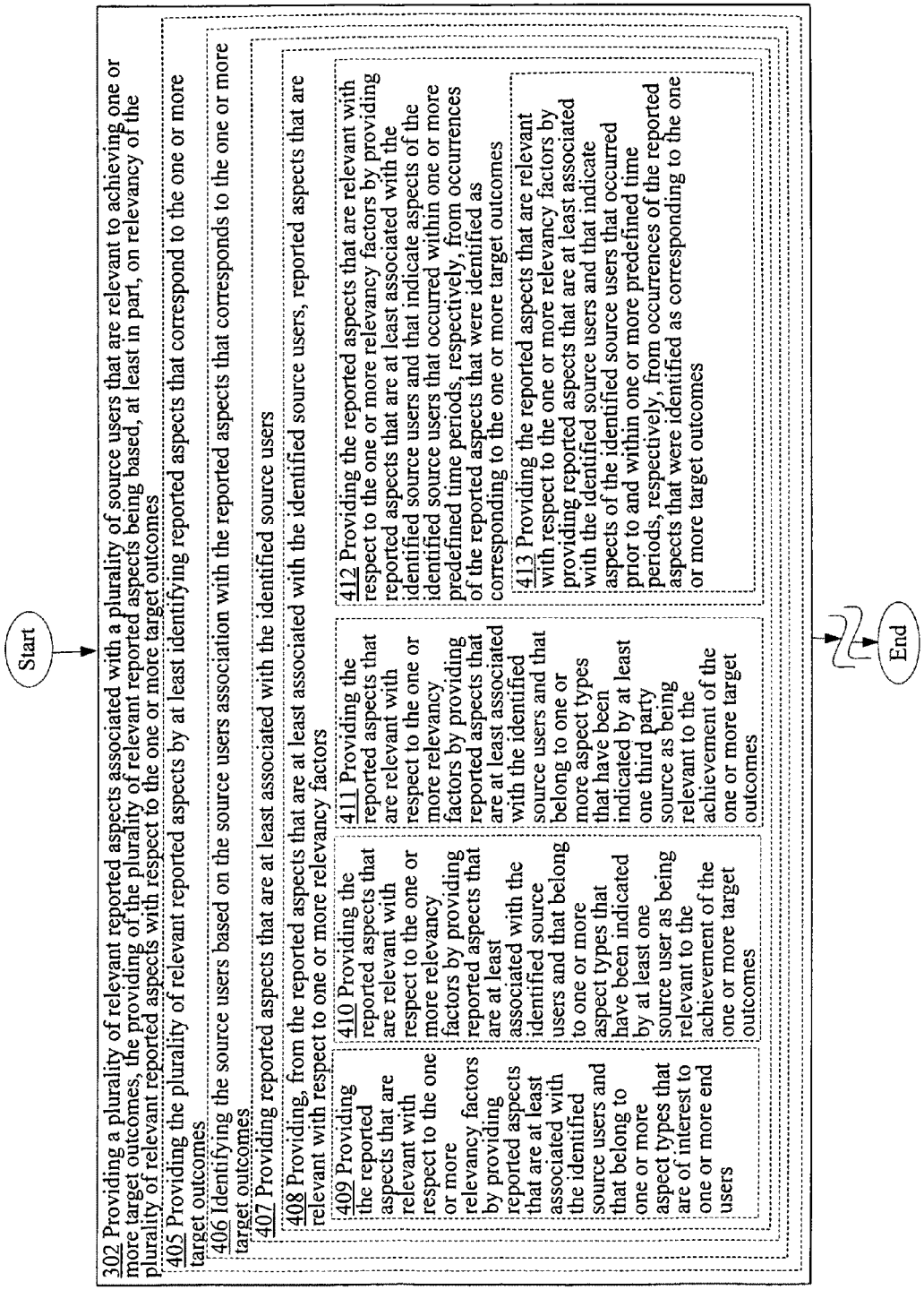
FIG. 4b is a high-level logic flowchart of a process depicting alternate implementations of the relevant reported aspect providing operation 302 of FIG. 3.

In the same or different implementations, the relevant reported aspect providing operation 302 of FIG. 3 may include one or more operations to determine or identify the plurality of relevant reported aspects 14. For example, in some implementations, the relevant reported aspect providing operation 302 of FIG. 3 may include an operation 405 for providing the plurality of relevant reported aspects by at least identifying reported aspects that correspond to the one or more target outcomes as depicted in FIG. 4b. For instance, the relevant reported aspect providing module 102 including the "target outcome corresponding reported aspect identifying" module 208 of the computing device 10 providing the plurality of relevant reported aspects 14 by at least identifying reported aspects 13 (which may be stored in a memory 116 and/or located at one or more network sites such as at the one or more local source user devices 20* or at the one or more network servers 60) that correspond (e.g., equivalent or substantially equivalent) to the one or more target outcomes.

Operation 405, in turn, may further include one or more additional operations in various alternative implementations. For example, in some implementations, operation 405 may include an operation 406 for identifying the source users based on the source users association with the reported aspects that corresponds to the one or more target outcomes as depicted in FIG. 4b. For instance, the source user identifying module 210 (see FIG. 2a) of the computing device 10 identifying the source users 2* based on the source users 2*association with the reported aspects (e.g., source users 2* reporting that they had achieved an A1C score, an indication of blood glucose level, of 6.2 or 6.0) that corresponds to the one or more target outcomes (e.g., A1C score of 6.2 or lower).

In some implementations, operation 406 may further include an operation 407 for providing reported aspects that are at least associated with the identified source users as depicted in FIG. 4b. For instance, the "identified source user associated reported aspect providing" module 212 (see FIG. 2a) of the computing device 10 providing reported aspects 13 that are at least associated with the identified source users 2*. In other words, providing reported aspects 13 that indicate specific aspects of the identified source users 2*.

In some implementations, operation 407 may further include an operation 408 for providing, from the reported aspects that are at least associated with the identified source users, reported aspects that are relevant with respect to one or more relevancy factors as depicted in FIG. 4b. For instance, the relevancy factor relevant reported aspect providing module 214 (see FIG. 2a) of the computing device 10 providing, from the reported aspects 13 that are at least associated with the identified source users 2*, reported aspects 13 (e.g., relevant reported aspects 14) that are relevant with respect to one or more relevancy factors.

In various implementations, operation 408 may further include one or more additional operations including, for example, an operation 409 for providing the reported aspects that are relevant with respect to the one or more relevancy factors by providing reported aspects that are at least associated with the identified source users and that belong to one or more aspect types that are of interest to one or more end users as depicted in FIG. 4b. For instance, the relevancy factor relevant reported aspect providing module 214 of the computing device 10 providing the reported aspects 13 that are relevant with respect to the one or more relevancy factors by providing reported aspects 13 (e.g., relevant reported aspects 14) that are at least associated with the identified source users 2* and that belong to one or more aspect types that are of interest to one or more end users 4*.

In the same or different implementations, operation 408 may include an operation 410 for providing the reported aspects that are relevant with respect to the one or more relevancy factors by providing reported aspects that are at least associated with the identified source users and that belong to one or more aspect types that have been indicated by at least one source user as being relevant to the achievement of the one or more target outcomes as depicted in FIG. 4b. For instance, the relevancy factor relevant reported aspect providing module 214 of the computing device 10 providing the reported aspects 13 that are relevant with respect to the one or more relevancy factors by providing reported aspects 13 (e.g., relevant reported aspects 14) that are at least associated with the identified source users 2* and that belong to one or more aspect types that have been indicated by at least one source user 2* as being relevant to the achievement of the one or more target outcomes.

In the same or different implementations, operation 408 may include an operation 411 for providing the reported aspects that are relevant with respect to the one or more relevancy factors by providing reported aspects that are at least associated with the identified source users and that belong to one or more aspect types that have been indicated by at least one third party source as being relevant to the achievement of the one or more target outcomes as depicted in FIG. 4b. For instance, the relevancy factor relevant reported aspect providing module 214 of the computing device 10 providing the reported aspects 13 that are relevant with respect to the one or more relevancy factors by providing reported aspects 13 (e.g., relevant reported aspects 14) that are at least associated with the identified source users 2* and that belong to one or more aspect types that have been indicated by at least one third party source (e.g., a publication, a peer-reviewed research publication, a third party 6, and so forth) as being relevant to the achievement of the one or more target outcomes.

In the same or different implementations, operation 408 may include an operation 412 for providing the reported aspects that are relevant with respect to the one or more relevancy factors by providing reported aspects that are at least associated with the identified source users and that indicate aspects of the identified source users that occurred within one or more predefined time periods, respectively, from occurrences of the reported aspects that were identified as corresponding to the one or more target outcomes as depicted in FIG. 4b. For instance, the relevancy factor relevant reported aspect providing module 214 of the computing device 10 providing the reported aspects 13 that are relevant with respect to the one or more relevancy factors by providing reported aspects 13 (e.g., cease consuming caffeine and increase exercise activities) that are at least associated with the identified source users 2* and that indicate aspects of the identified source users 2* that occurred within one or more predefined time periods (e.g., two months), respectively, from occurrences of the reported aspects 13 (e.g., lowering blood pressure) that were identified as corresponding to the one or more target outcomes (e.g., lowering blood pressure). The purpose here is to, for example, exclude from consideration those reported aspects 13 that indicate aspects of the identified source users 2* that occurred well before or well after the achievement of the one or more target outcomes by the identified source user 2*. In various implementations, the predefined time periods may be set by a source user 2*, by an end user 4*, or by a third party 6 (e.g., a physician, a content provider, a network service provider, and so forth).

In various implementations, operation 412 may include an operation 413 for providing the reported aspects that are relevant with respect to the one or more relevancy factors by providing reported aspects that are at least associated with the identified source users and that indicate aspects of the identified source users that occurred prior to and within one or more predefined time periods, respectively, from occurrences of the reported aspects that were identified as corresponding to the one or more target outcomes as depicted in FIG. 4b. For instance, the relevancy factor relevant reported aspect providing module 214 of the computing device 10 providing the reported aspects 13 that are relevant with respect to the one or more relevancy factors by providing reported aspects 13 (e.g., jogging) that are at least associated with the identified source users 2* and that indicate aspects of the identified source users 2* that occurred prior to and within one or more predefined time periods (e.g., 2 weeks), respectively, from occurrences of the reported aspects 13 (e.g., getting 8 hours of continuous and restful sleep) that were identified as corresponding to the one or more target outcomes (e.g., 8 hours of continuous and restful sleep).

Figure 4C:
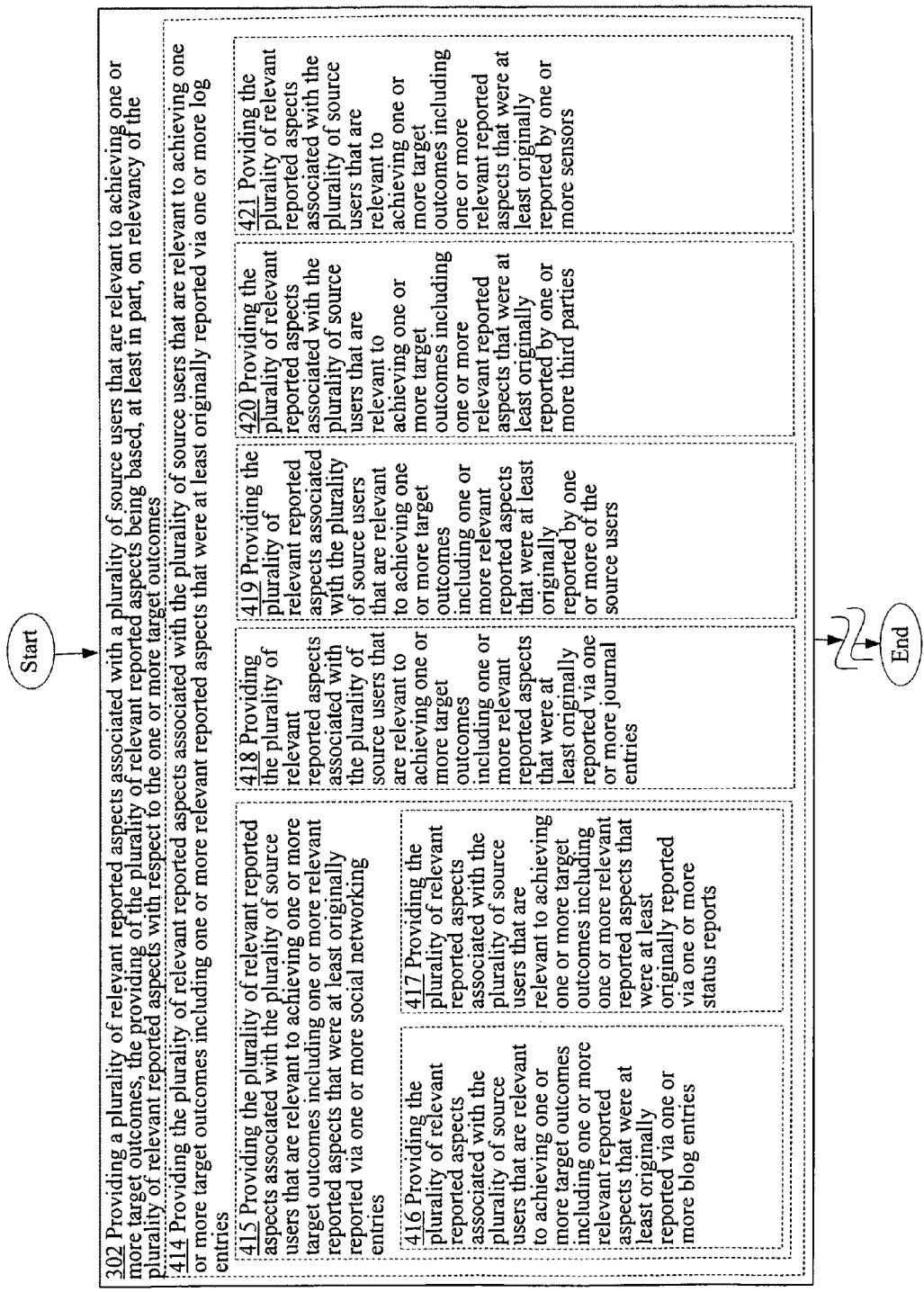
FIG. 4c is a high-level logic flowchart of a process depicting alternate implementations of the relevant reported aspect providing operation 302 of FIG. 3.

The plurality of relevant reported aspects 14 that may be provided through the relevant reported aspect providing operation 302 of FIG. 3 may have been originally reported by a variety of different ways. For example, in some implementations, the relevant reported aspect providing operation 302 of FIG. 3 may include an operation 414 for providing the plurality of relevant reported aspects associated with the plurality of source users that are relevant to achieving one or more target outcomes including one or more relevant reported aspects that were at least originally reported via one or more log entries as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported via one or more log entries (e.g., as received by, for example, the log entry receiving module 108 of the computing device 10).

In various implementations, operation 414 may include one or more additional operations. For example, in some cases, operation 414 may further include an operation 415 for providing the plurality of relevant reported aspects associated with the plurality of source users that are relevant to achieving one or more target outcomes including one or more relevant reported aspects that were at least originally reported via one or more social networking entries as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported via one or more social networking entries (e.g., as received by, for example, the social networking entry receiving module 110 of the computing device 10).

In various implementations, operation 415 may further include an operation 416 for providing the plurality of relevant reported aspects associated with the plurality of source users that are relevant to achieving one or more target outcomes including one or more relevant reported aspects that were at least originally reported via one or more blog entries as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported via one or more blog entries such as one or more microblog entries (e.g., as received by, for example, the blog entry receiving module 111 of the computing device 10).

In the same or different implementations, operation 415 may include an operation 417 for providing the plurality of relevant reported aspects associated with the plurality of source users that are relevant to achieving one or more target outcomes including one or more relevant reported aspects that were at least originally reported via one or more status reports as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported via one or more status reports such as one or more social networking status reports (e.g., as received by, for example, the status report receiving module 112 of the computing device 10).

In some implementations, operation 414 may include an operation 418 for providing the plurality of relevant reported aspects associated with the plurality of source users that are relevant to achieving one or more target outcomes including one or more relevant reported aspects that were at least originally reported via one or more journal entries as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported via one or more journal entries (e.g., as received by, for example, the journal entry receiving module 114 of the computing device 10).

In the same or different implementations, operation 414 may include an operation 419 for providing the plurality of relevant reported aspects associated with the plurality of source users that are relevant to achieving one or more target outcomes including one or more relevant reported aspects that were at least originally reported by one or more of the source users as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported by one or more of the source users 2*.

In the same or different implementations, operation 414 may further include an operation 420 for providing the plurality of relevant reported aspects associated with the plurality of source users that are relevant to achieving one or more target outcomes including one or more relevant reported aspects that were at least originally reported by one or more third parties as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported by one or more third parties 6.

In some implementations, operation 414 may include an operation 421 for providing the plurality of relevant reported aspects associated with the plurality of source users that are relevant to achieving one or more target outcomes including one or more relevant reported aspects that were at least originally reported by one or more sensors as depicted in FIG. 4c. For instance, the relevant reported aspect providing module 102 of the computing device 10 providing the plurality of relevant reported aspects 14 associated with the plurality of source users 2* that are relevant to achieving one or more target outcomes including one or more relevant reported aspects 14 that were at least originally reported by one or more sensors 240 (which may be located at one or more local source user devices 20*, at one or more sensor integrated devices 40, and/or at the computing device 10).

Figure 4D:
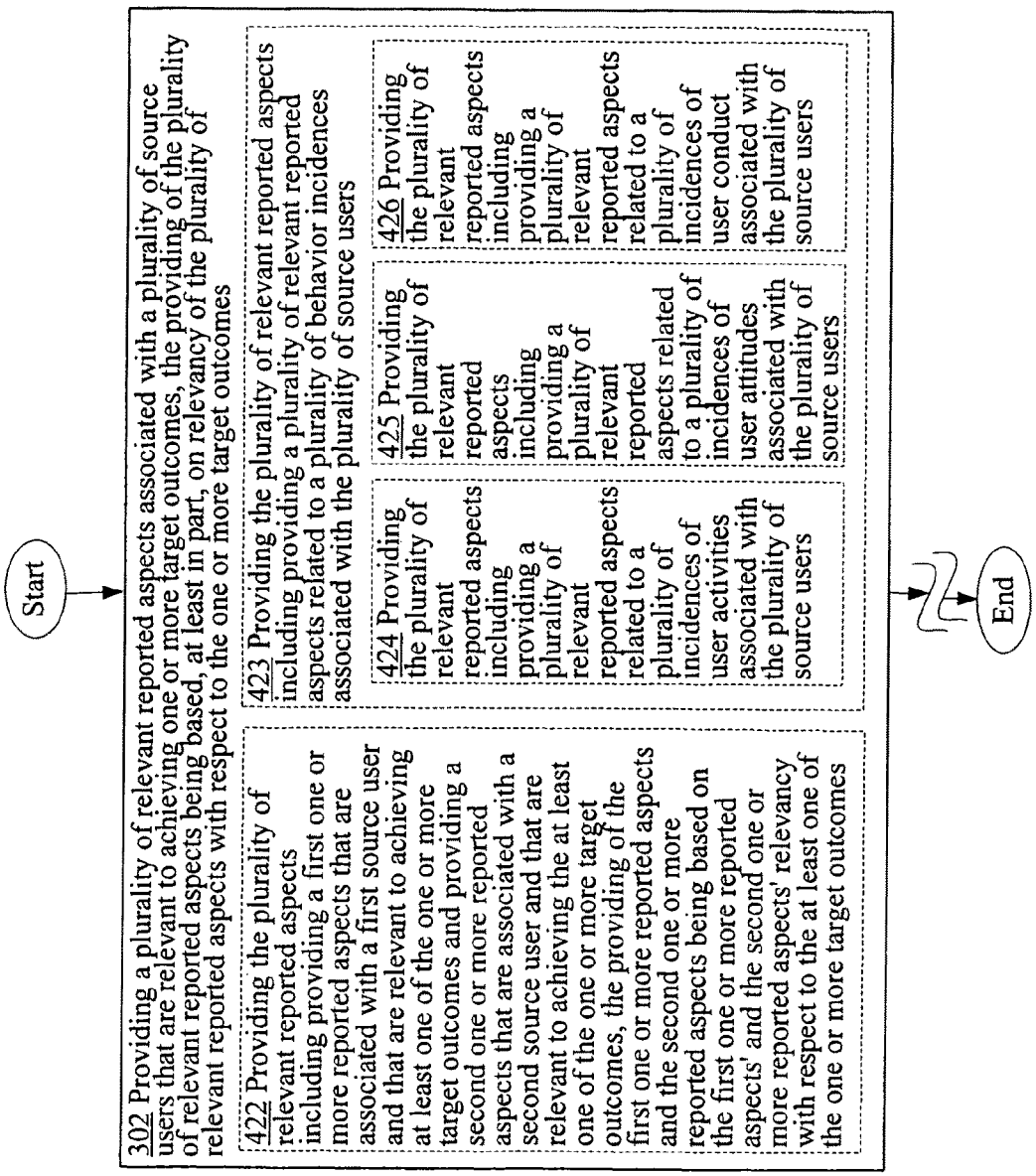
FIG. 4d is a high-level logic flowchart of a process depicting alternate implementations of the relevant reported aspect providing operation 302 of FIG. 3.

In various implementations, the relevant reported aspect providing operation 302 of FIG. 3 may include an operation 422 for providing the plurality of relevant reported aspects including providing a first one or more reported aspects that are associated with a first source user and that are relevant to achieving at least one of the one or more target outcomes and providing a second one or more reported aspects that are associated with a second source user and that are relevant to achieving the at least one of the one or more target outcomes, the providing of the first one or more reported aspects and the second one or more reported aspects being based on the first one or more reported aspects' and the second one or more reported aspects' relevancy with respect to the at least one of the one or more target outcomes as depicted in FIG. 4d. For instance, the relevant reported aspect providing module 102 of the computing device 10 providing the plurality of relevant reported aspects 14 including providing a first one or more reported aspects 13 that are associated with a first source user 2a and that are relevant to achieving at least one of the one or more target outcomes and providing a second one or more reported aspects 13 that are associated with a second source user 2b and that are relevant to achieving the at least one of the one or more target outcomes, the providing of the first one or more reported aspects 13 and the second one or more reported aspects 13 being based on relevancy of the first one or more reported aspects 13 and the second one or more reported aspects 13 with respect to the at least one of the one or more target outcomes.

The plurality of relevant reported aspects 14 that may be provided through the relevant reported aspect providing operation 302 of FIG. 3 may include a variety of aspects related to the plurality of source users 2*. For example, in some implementations, relevant reported aspect providing operation 302 may include an operation 423 for providing the plurality of relevant reported aspects including providing a plurality of relevant reported aspects related to a plurality of behavior incidences associated with the plurality of source users as depicted in FIG. 4d. For instance, the relevant reported aspect providing module 102 of the computing device 10 providing the plurality of relevant reported aspects 14 including providing a plurality of relevant reported aspects 14 related to a plurality of behavior incidences (e.g., dietary activities, exercise activities, social behavior, and so forth) associated with the plurality of source users 2*.

In some implementations, operation 423 may further include an operation 424 for providing the plurality of relevant reported aspects including providing a plurality of relevant reported aspects related to a plurality of incidences of user activities associated with the plurality of source users as depicted in FIG. 4d. For instance, the relevant reported aspect providing module 102 of the computing device 10 providing the plurality of relevant reported aspects 14 including providing a plurality of relevant reported aspects 14 related to a plurality of incidences of user activities (e.g., consuming a particular medication or food, sleeping in a particular type of bed, reading a particular book, and so forth) associated with the plurality of source users 2*.

In the same or different implementations, operation 423 may include an operation 425 for providing the plurality of relevant reported aspects including providing a plurality of relevant reported aspects related to a plurality of incidences of user attitudes associated with the plurality of source users as depicted in FIG. 4d. For instance, the relevant reported aspect providing module 102 of the computing device 10 providing the plurality of relevant reported aspects 14 including providing a plurality of relevant reported aspects 14 related to a plurality of incidences of user attitudes (e.g., disdain, loving or caring, and so forth) associated with the plurality of source users 2*.

In the same or different implementations, operation 423 may include an operation 426 for providing the plurality of relevant reported aspects including providing a plurality of relevant reported aspects related to a plurality of incidences of user conduct associated with the plurality of source users as depicted in FIG. 4d. For instance, the relevant reported aspect providing module 102 of the computing device 10 providing the plurality of relevant reported aspects 14 including providing a plurality of relevant reported aspects 14 related to a plurality of incidences of user conduct (e.g., treating subordinates as equal, driving a friend's car carefully, and so forth) associated with the plurality of source users 2*.

Figure 4E:
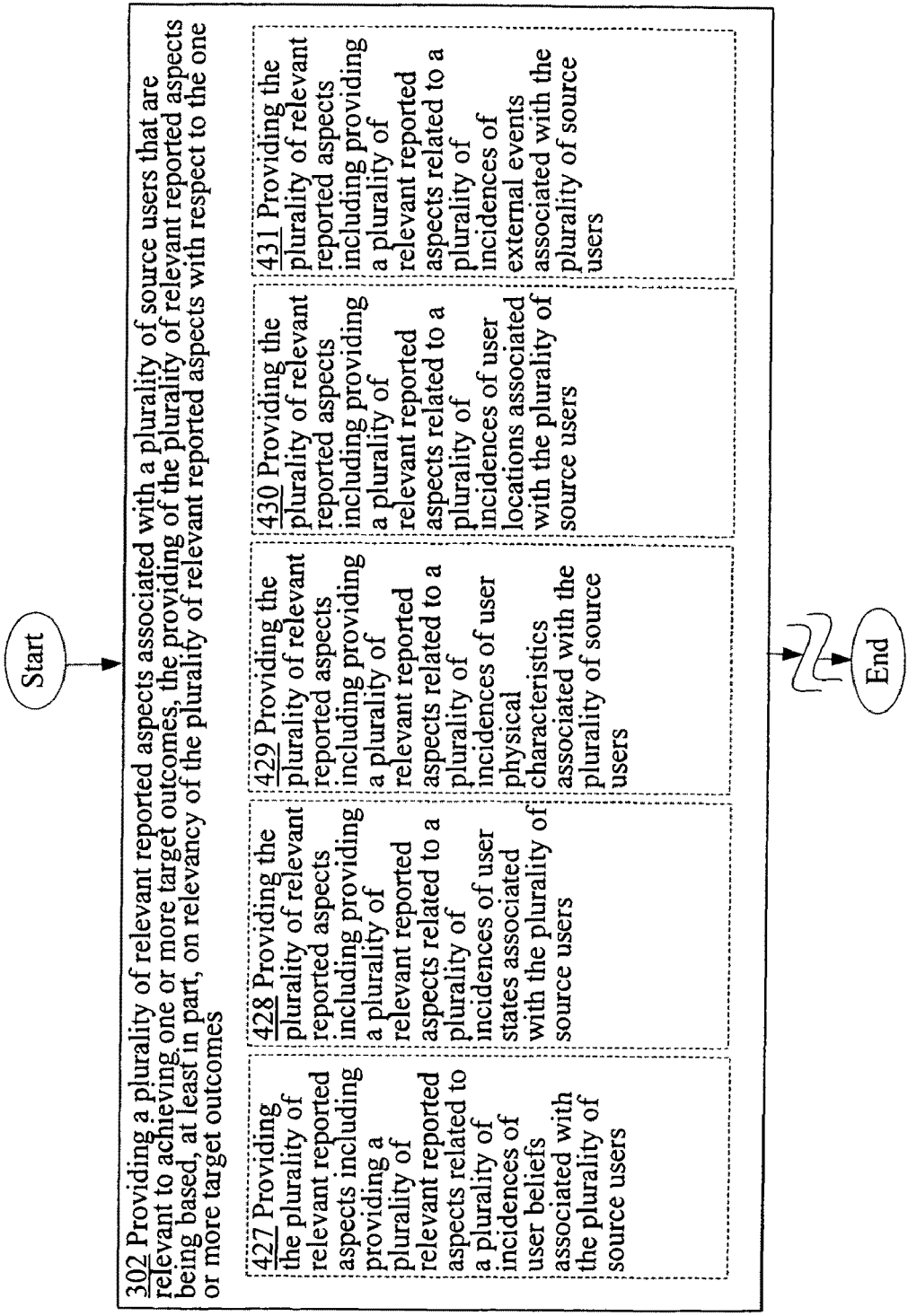
FIG. 4e is a high-level logic flowchart of a process depicting alternate implementations of the relevant reported aspect providing operation 302 of FIG. 3.

In some implementations, the relevant reported aspect providing operation 302 of FIG. 3 may include an operation 427 for providing the plurality of relevant reported aspects including providing a plurality of relevant reported aspects related to a plurality of incidences of user beliefs associated with the plurality of source users as depicted in FIG. 4e. For instance, the relevant reported aspect providing module 102 of the computing device 10 providing the plurality of relevant reported aspects 14 including providing a plurality of relevant reported aspects 14 related to a plurality of incidences of user beliefs (e.g., dietary beliefs, social or religious beliefs, superstitious beliefs, and so forth) associated with the plurality of source users 2*.

In the same or different implementations, the relevant reported aspect providing operation 302 may include an operation 428 for providing the plurality of relevant reported aspects including providing a plurality of relevant reported aspects related to a plurality of incidences of user states associated with the plurality of source users as depicted in FIG. 4e. For instance, the relevant reported aspect providing module 102 of the computing device 10 providing the plurality of relevant reported aspects 14 including providing a plurality of relevant reported aspects 14 related to a plurality of incidences of user states (e.g., marital state, academic state, social state, health or fitness state, mental state, physical state, and so forth) associated with the plurality of source users 2*.

In the same or different implementations, the relevant reported aspect providing operation 302 may include an operation 429 for providing the plurality of relevant reported aspects including providing a plurality of relevant reported aspects related to a plurality of incidences of user physical characteristics associated with the plurality of source users as depicted in FIG. 4e. For instance, the relevant reported aspect providing module 102 of the computing device 10 providing the plurality of relevant reported aspects 14 including providing a plurality of relevant reported aspects 14 related to a plurality of incidences of user physical characteristics (e.g., body fat level, hair color, and so forth) associated with the plurality of source users 2*.

In the same or different implementations, the relevant reported aspect providing operation 302 may include an operation 430 for providing the plurality of relevant reported aspects including providing a plurality of relevant reported aspects related to a plurality of incidences of user locations associated with the plurality of source users as depicted in FIG. 4e. For instance, the relevant reported aspect providing module 102 of the computing device 10 providing the plurality of relevant reported aspects 14 including providing a plurality of relevant reported aspects 14 related to a plurality of incidences of user locations associated with the plurality of source users 2*.

In the same or different implementations, the relevant reported aspect providing operation 302 may include an operation 431 for providing the plurality of relevant reported aspects including providing a plurality of relevant reported aspects related to a plurality of incidences of external events associated with the plurality of source users as depicted in FIG. 4e. For instance, the relevant reported aspect providing module 102 of the computing device 10 providing the plurality of relevant reported aspects 14 including providing a plurality of relevant reported aspects 14 related to a plurality of incidences of external events (e.g., external environmental or atmospheric conditions) associated with the plurality of source users 2*.

Figure 5A:
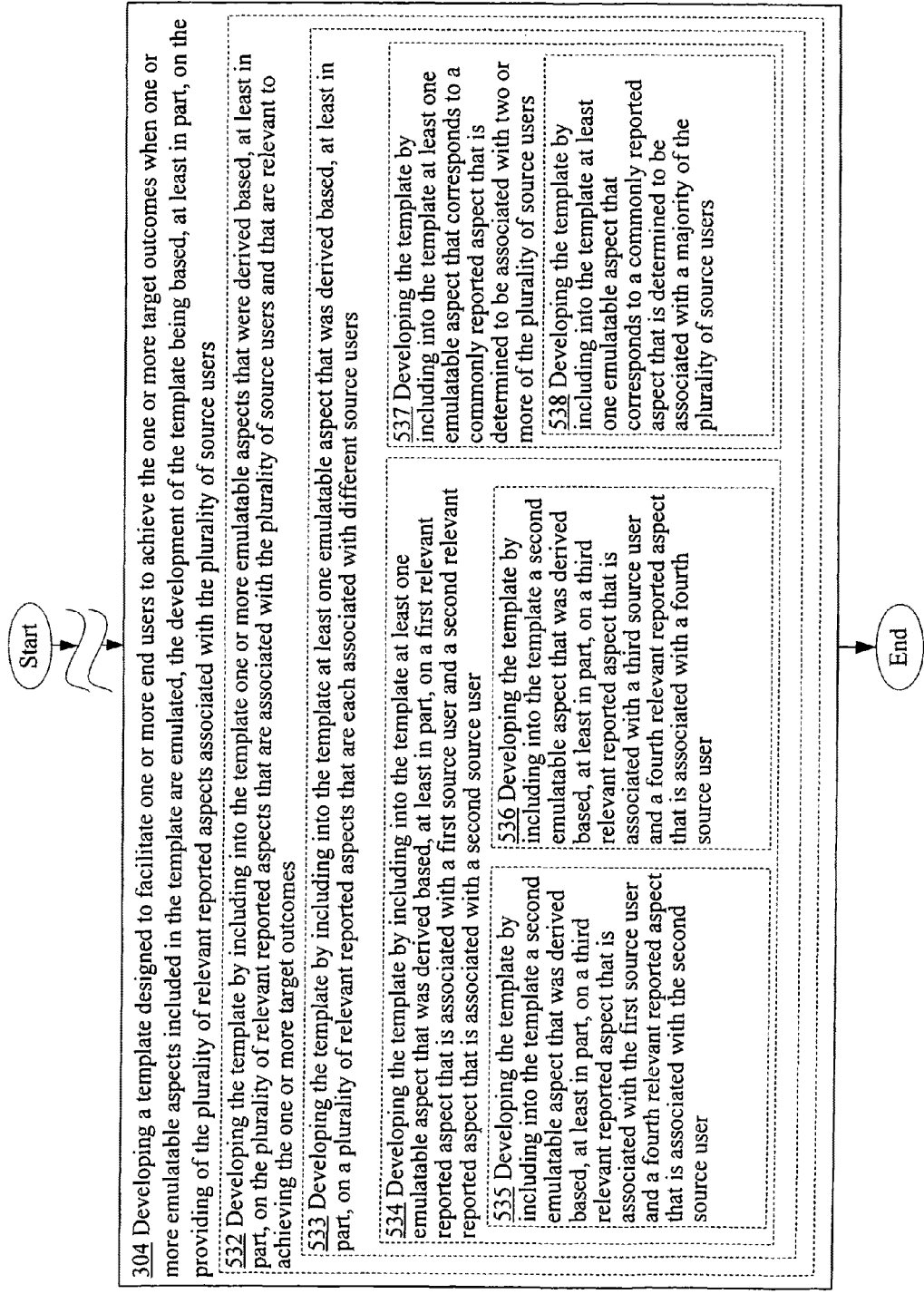
FIG. 5a is a high-level logic flowchart of a process depicting alternate implementations of the template developing operation 304 of FIG. 3.

Referring back to FIG. 3, the template developing operation 304 may be implemented in a number of different ways in various alternative implementations. For example, in some implementations, the template developing operation 304 may include an operation 532 for developing the template by including into the template one or more emulatable aspects that were derived based, at least in part, on the plurality of relevant reported aspects that are associated with the plurality of source users and that are relevant to achieving the one or more target outcomes as depicted in FIG. 5a. For instance, the template developing module 104 of the computing device 10 developing the template 16 by having the emulatable aspect including module 216 (see FIG. 2b) include into the template 16 one or more emulatable aspects that were derived (e.g., as derived by, for example, the emulatable aspect deriving module 218) based, at least in part, on the plurality of relevant reported aspects 14 that are associated with the plurality of source users 2* and that are relevant to achieving one or more target outcomes.

In various implementations, operation 532 may further include an operation 533 for developing the template by including into the template at least one emulatable aspect that was derived based, at least in part, on a plurality of relevant reported aspects that are each associated with different source users as depicted in FIG. 5a. For instance, the template developing module 104 of the computing device 10 developing the template 16 by having the emulatable aspect including module 216 include into the template 16 at least one emulatable aspect that was derived (e.g., as derived by, for example, the emulatable aspect deriving module 218) based, at least in part, on a plurality of relevant reported aspects 14 that are each associated with different source users 2*.

In some cases, operation 533 may further include an operation 534 for developing the template by including into the template at least one emulatable aspect that was derived based, at least in part, on a first relevant reported aspect that is associated with a first source user and a second relevant reported aspect that is associated with a second source user as depicted in FIG. 5a. For instance, the template developing module 104 of the computing device 10 developing the template 16 by having the emulatable aspect including module 216 (see FIG. 2b) include into the template 16 at least one emulatable aspect (e.g., jogging for 45 minutes) that was derived (e.g., as derived by, for example, the emulatable aspect deriving module 218) based, at least in part, on a first relevant reported aspect (e.g., jogging for 55 minutes) that is associated with a first source user 2a and a second relevant reported aspect (e.g., jogging for 35 minutes) that is associated with a second source user 2b.

In some implementations, operation 534 may further include one or more additional operations including, for example, an operation 535 for developing the template by including into the template a second emulatable aspect that was derived based, at least in part, on a third relevant reported aspect that is associated with the first source user and a fourth relevant reported aspect that is associated with the second source user as depicted in FIG. 5a. For instance, the template developing module 104 of the computing device 10 developing the template 16 by having the emulatable aspect including module 216 include into the template 16 a second emulatable aspect (e.g., jogging at a moderate pace) that was derived (e.g., as derived by, for example, the emulatable aspect deriving module 218) based, at least in part, on a third relevant reported aspect (e.g., jogging at a very quick pace) that is associated with the first source user 2a and a fourth relevant reported aspect (e.g., jogging at a very slow pace) that is associated with the second source user 2b.

In the same or different implementations, operation 534 may include an operation 536 for developing the template by including into the template a second emulatable aspect that was derived based, at least in part, on a third relevant reported aspect that is associated with a third source user and a fourth relevant reported aspect that is associated with a fourth source user as depicted in FIG. 5a. For instance, the template developing module 104 of the computing device 10 developing the template 16 by having the emulatable aspect including module 216 include into the template 16 a second emulatable aspect (e.g., rowing for one hour) that was derived (e.g., as derived by, for example, the emulatable aspect deriving module 218) based, at least in part, on a third relevant reported aspect (e.g., rowing for one hour) that is associated with a third source user 2c and a fourth relevant reported aspect (e.g., swimming for one hour) that is associated with a fourth source user 2d.

Note that in this example, the second emulatable aspect that was included into the template 16 was the same as the third relevant reported aspect (of the third source user 2c) completely different from the fourth relevant reported aspect (of the fourth source user 2d). In cases like this, certain factors or rules may be considered in resolving conflicts between relevant reported aspects in order to, for example, determine the second emulatable aspect. For example, there may be a rule that says that the most commonly executed reported aspect be used in order to determine an emulatable aspect (e.g., in the above example, the first source user 2a and the second source user 2b may also have reported rowing for one hour). In another example, relevant reported aspects of, for example, a first group of source users 2* may be given more weight than the relevant reported aspects of a second group of source users 2* because the first group of source users 2* may have similar traits (e.g., physical traits, health traits, intellectual traits, and so forth) as the end users 4*. Of course, those skilled in the art will recognize that there are many other tie breaker rules that may be used in order to resolve conflicts between relevant reported aspects.

In various implementations, operation 533 for developing a template 16 by including into the template 16 at least one emulatable aspect may include an operation 537 for developing the template by including into the template at least one emulatable aspect that corresponds to a commonly reported aspect that is determined to be associated with two or more of the plurality of source users as depicted in FIG. 5a. For instance, the template developing module 104 of the computing device 10 developing the template 16 by having the emulatable aspect including module 216 include into the template 16 at least one emulatable aspect that corresponds to a commonly reported aspect (e.g., a source user aspect that is reported by, for example, more than one source user 2*) that is determined to be associated with two or more of the plurality of source users 2* (e.g., as determined by the commonly reported aspect determining module 220).

In some implementations, operation 537 may further include an operation 538 for developing the template by including into the template at least one emulatable aspect that corresponds to a commonly reported aspect that is determined to be associated with a majority of the plurality of source users as depicted in FIG. 5a. For instance, the template developing module 104 of the computing device 10 developing the template 16 by having the emulatable aspect including module 216 include into the template 16 at least one emulatable aspect that corresponds to a commonly reported aspect that is determined to be associated with a majority of the plurality of source users 2* (e.g., as determined by the commonly reported aspect determining module 220).

Figure 5B:
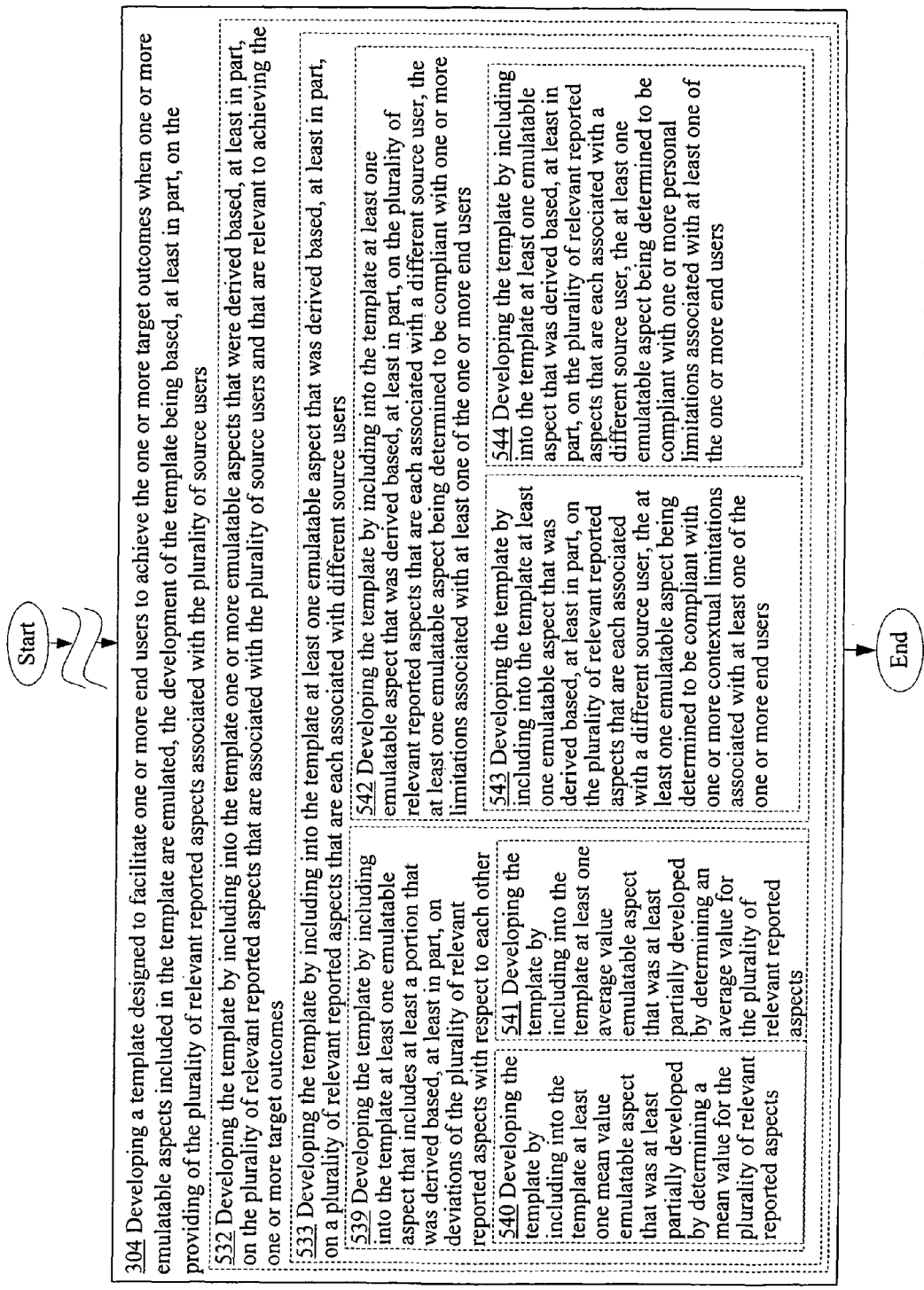
FIG. 5b is a high-level logic flowchart of a process depicting alternate implementations of the template developing operation 304 of FIG. 3.

In various implementations, the operation 533 for developing a template 16 by including into the template 16 at least one emulatable aspect may include an operation 539 for developing the template by including into the template at least one emulatable aspect that includes at least a portion that was derived based, at least in part, on deviations of the plurality of relevant reported aspects with respect to each other as depicted in FIG. 5b. For instance, the template developing module 104 of the computing device 10 developing the template 16 by having the emulatable aspect including module 216 include into the template 16 at least one emulatable aspect (e.g., swimming for 30 minutes) that includes at least a portion (e.g., 30 minutes) that was derived based, at least in part, on deviations of the plurality of relevant reported aspects 14 with respect to each other (e.g., as determined by, for example, the deviation determining module 222).

In some implementations, operation 539 may further include an operation 540 for developing the template by including into the template at least one mean value emulatable aspect that was at least partially developed by determining a mean value for the plurality of relevant reported aspects as depicted in FIG. 5b. For instance, the template developing module 104 of the computing device 10 developing the template 16 by having the emulatable aspect including module 216 include into the template 16 at least one mean value emulatable aspect that was at least partially developed by determining a mean value for the plurality of relevant reported aspects 14 (e.g., as determined by, for example, the mean value determining module 224). For example, in the above swimming example, determining the mean value for the amount of time that the source users 2* reported swimming. Note that in some cases it may also be possible to obtain a mean value for variables that may not be considered quantifiable variables such as, for example, "jogging" (e.g., a mean value can be obtained from, for example, jogging at a fast pace, jogging at a moderate pace, or jogging at a slow pace).

In the same or different implementations, operation 539 may include an operation 541 for developing the template by including into the template at least one average value emulatable aspect that was at least partially developed by determining an average value for the plurality of relevant reported aspects as depicted in FIG. 5b. For instance, the template developing module 104 of the computing device 10 developing the template 16 by having the emulatable aspect including module 216 include into the template 16 at least one average value emulatable aspect that was at least partially developed by determining an average value for the plurality of relevant reported aspects 14 (e.g., as determined by, for example, the average value determining module 226).

In some cases, operation 533 for developing a template 16 by including into the template 16 at least one emulatable aspect may include an operation 542 for developing the template by including into the template at least one emulatable aspect that was derived based, at least in part, on the plurality of relevant reported aspects that are each associated with a different source user, the at least one emulatable aspect being determined to be compliant with one or more limitations associated with at least one of the one or more end users as depicted in FIG. 5b. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with (e.g., not violating) one or more limitations associated with at least one of the one or more end users 4*.

In some implementations, operation 542 may further include an operation 543 for developing the template by including into the template at least one emulatable aspect that was derived based, at least in part, on the plurality of relevant reported aspects that are each associated with a different source user, the at least one emulatable aspect being determined to be compliant with one or more contextual limitations associated with at least one of the one or more end users as depicted in FIG. 5b. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more contextual limitations (e.g., logistical limitations such as no or limited access to a swimming pool, a car, or a particular text book) associated with at least one of the one or more end users 4*.

In the same or different implementations, operation 542 may include an operation 544 for developing the template by including into the template at least one emulatable aspect that was derived based, at least in part, on the plurality of relevant reported aspects that are each associated with a different source user, the at least one emulatable aspect being determined to be compliant with one or more personal limitations associated with at least one of the one or more end users as depicted in FIG. 5b. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more personal limitations (e.g., dietary or religious limitations) associated with at least one of the one or more end users 4*.

In the same or different implementations, operation 542 may include an operation 545 for developing the template by including into the template at least one emulatable aspect that was derived based, at least in part, on the plurality of relevant reported aspects that are each associated with a different source user, the at least one emulatable aspect being determined to be compliant with one or more physical limitations associated with at least one of the one or more end users as depicted in FIG. 5c. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more physical limitations (e.g., having severe arthritis) associated with at least one of the one or more end users 4*.

In the same or different implementations, operation 542 may include an operation 546 for developing the template by including into the template at least one emulatable aspect that was derived based, at least in part, on the plurality of relevant reported aspects that are each associated with a different source user, the at least one emulatable aspect being determined to be compliant with one or more medical or health limitations associated with at least one of the one or more end users as depicted in FIG. 5c. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more medical or health limitations (e.g., being lactose intolerant, being diabetic, or being in poor physical shape) associated with at least one of the one or more end users 4*.

In the same or different implementations, operation 542 may include an operation 547 for developing the template by including into the template at least one emulatable aspect that was derived based, at least in part, on the plurality of relevant reported aspects that are each associated with a different source user, the at least one emulatable aspect being determined to be compliant with one or more user state limitations associated with at least one of the one or more end users as depicted in FIG. 5c. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more user state limitations (e.g., being married, being unemployed, or being mentally or physically fatigued) associated with at least one of the one or more end users 4*.

In the same or different implementations, operation 542 may include an operation 548 for developing the template by including into the template at least one emulatable aspect that was derived based, at least in part, on the plurality of relevant reported aspects that are each associated with a different source user, the at least one emulatable aspect being determined to be compliant with one or more legal or regulatory limitations associated with at least one of the one or more end users as depicted in FIG. 5c. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more legal or regulatory limitations (e.g., local drug regulations) associated with at least one of the one or more end users 4*.

Figure 5D:
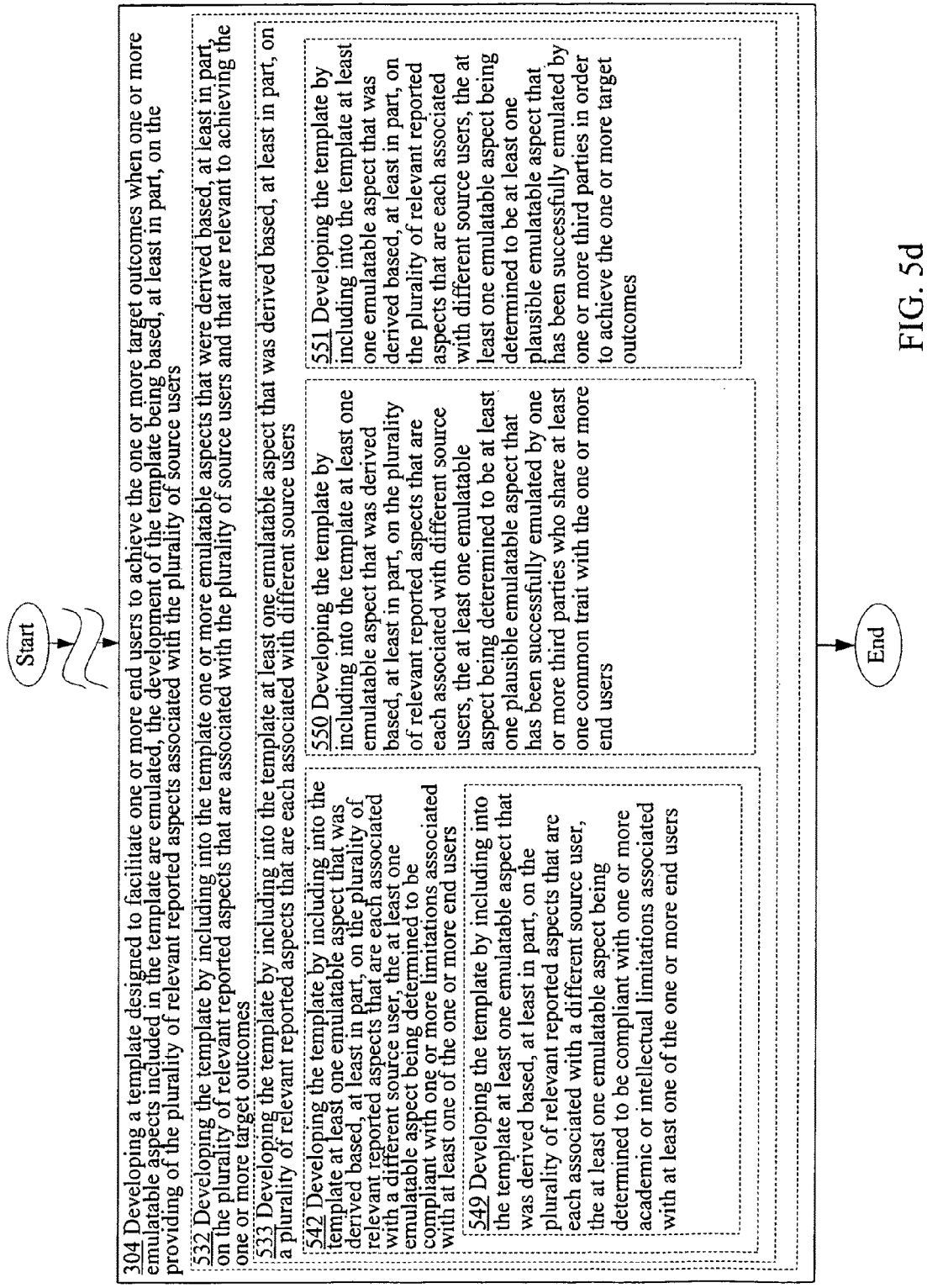
FIG. 5d is a high-level logic flowchart of a process depicting alternate implementations of the template developing operation 304 of FIG. 3.

In the same or different implementations, operation 542 may include an operation 549 for developing the template by including into the template at least one emulatable aspect that was derived based, at least in part, on the plurality of relevant reported aspects that are each associated with a different source user, the at least one emulatable aspect being determined to be compliant with one or more academic or intellectual limitations associated with at least one of the one or more end users as depicted in FIG. 5d. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with a different source user 2*, the at least one emulatable aspect being determined (e.g., as determined by the compliant determining module 228) to be compliant with one or more academic or intellectual limitations (e.g., lacks particular educational or training background) associated with at least one of the one or more end users 4*.

In the same or different implementations, operation 533 may include an operation 550 for developing the template by including into the template at least one emulatable aspect that was derived based, at least in part, on the plurality of relevant reported aspects that are each associated with different source users, the at least one emulatable aspect being determined to be at least one plausible emulatable aspect that has been successfully emulated by one or more third parties who share at least one common trait with the one or more end users as depicted in FIG. 5d. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with different source users 2*, the at least one emulatable aspect being determined (e.g., as determined by the plausible emulatable aspect determining module 230) to be at least one plausible emulatable aspect that has been successfully emulated by one or more third parties 6 who share at least one common trait (e.g., ethnicity or illness) with the one or more end users 4*.

In the same or different implementations, operation 533 may include an operation 551 for developing the template by including into the template at least one emulatable aspect that was derived based, at least in part, on the plurality of relevant reported aspects that are each associated with different source users, the at least one emulatable aspect being determined to be at least one plausible emulatable aspect that has been successfully emulated by one or more third parties in order to achieve the one or more target outcomes as depicted in FIG. 5d. For instance, the template developing module 104 of the computing device 10 developing the template 16 by having the emulatable aspect including module 216 include into the template 16 at least one emulatable aspect that was derived by the emulatable aspect deriving module 218 based, at least in part, on the plurality of relevant reported aspects 14* that are each associated with different source users 2*, the at least one emulatable aspect being determined (e.g., as determined by the plausible emulatable aspect determining module 230) to be at least one plausible emulatable aspect that has been successfully emulated by one or more third parties 6 in order to achieve the one or more target outcomes.

Figure 5E:
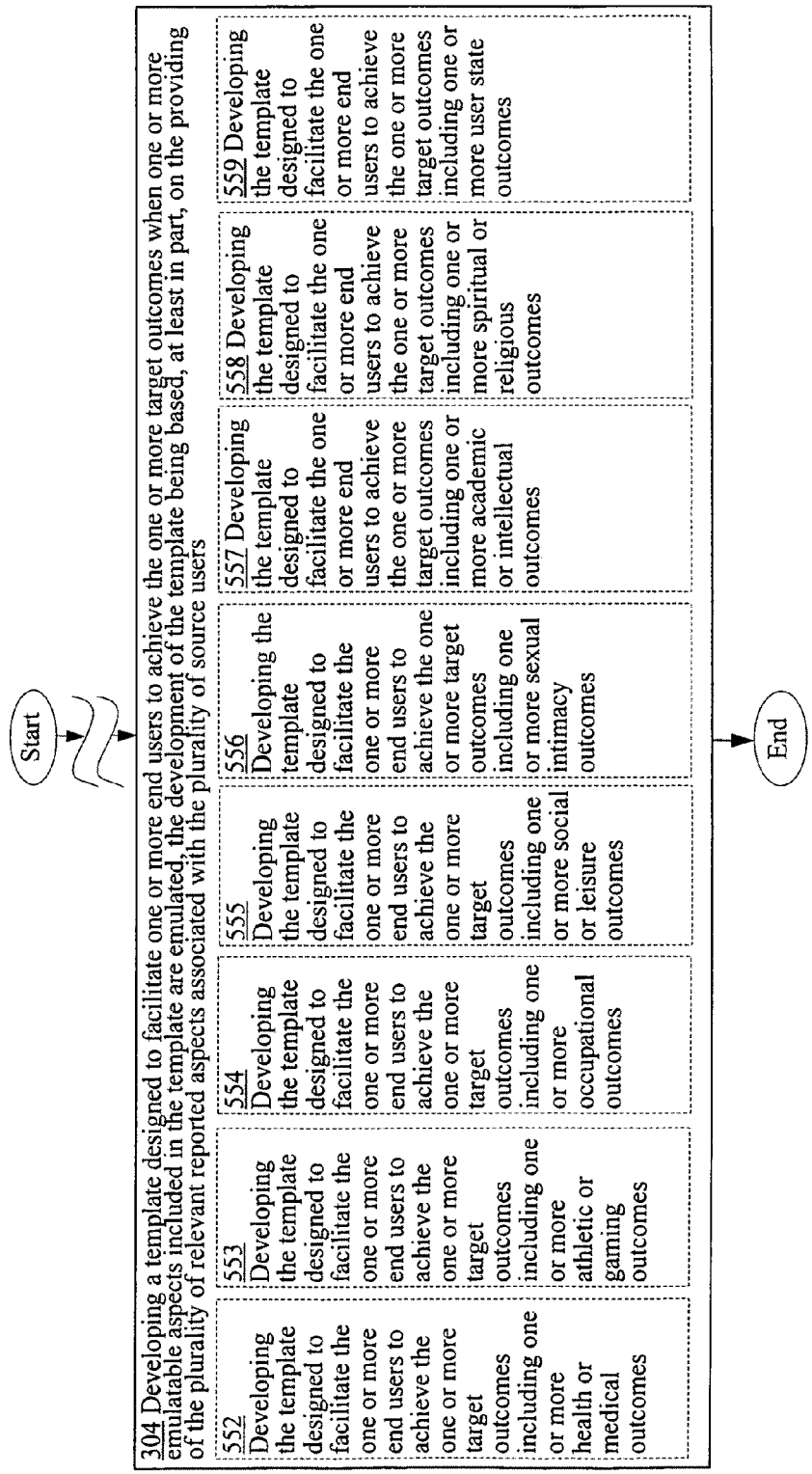
FIG. 5e is a high-level logic flowchart of a process depicting alternate implementations of the template developing operation 304 of FIG. 3.

In various implementations, the template 16 that is developed through the template developing operation 304 of FIG. 3 may be designed to facilitate achievement of any one or more of a variety of target outcomes. For example, in some implementations, the template developing operation 304 may include an operation 552 for developing the template designed to facilitate the one or more end users to achieve the one or more target outcomes including one or more health or medical outcomes as depicted in FIG. 5e. For instance, the template developing module 104 of the computing device 10 developing the template 16 designed to facilitate the one or more end users 4* to achieve the one or more target outcomes including one or more health or medical outcomes (e.g., losing weight, improve results of a medical treatment, reduce pain, reduce stress, reduce blood pressure or blood glucose levels, and so forth).

In the same or different implementations, the template developing operation 304 may include an operation 553 for developing the template designed to facilitate the one or more end users to achieve the one or more target outcomes including one or more athletic or gaming outcomes as depicted in FIG. 5e. For instance, the template developing module 104 of the computing device 10 developing the template 16 designed to facilitate the one or more end users 4* to achieve the one or more target outcomes including one or more athletic or gaming outcomes (e.g., win a tennis tournament, lower golf handicap, improve scores on an electronic game, and so forth).

In the same or different implementations, the template developing operation 304 may include an operation 554 for developing the template designed to facilitate the one or more end users to achieve the one or more target outcomes including one or more occupational outcomes as depicted in FIG. 5e. For instance, the template developing module 104 of the computing device 10 developing the template 16 designed to facilitate the one or more end users 4* to achieve the one or more target outcomes including one or more occupational outcomes (e.g., complete a work project, getting a new client, obtaining a promotion, and so forth).

In the same or different implementations, the template developing operation 304 may include an operation 555 for developing the template designed to facilitate the one or more end users to achieve the one or more target outcomes including one or more social or leisure outcomes as depicted in FIG. 5e. For instance, the template developing module 104 of the computing device 10 developing the template 16 designed to facilitate the one or more end users 4* to achieve the one or more target outcomes including one or more social or leisure outcomes (e.g., invited to be a member of an elite social organization, acquiring new friends, and so forth).

In the same or different implementations, the template developing operation 304 may include an operation 556 for developing the template designed to facilitate the one or more end users to achieve the one or more target outcomes including one or more sexual intimacy outcomes as depicted in FIG. 5e. For instance, the template developing module 104 of the computing device 10 developing the template 16 designed to facilitate the one or more end users 4* to achieve the one or more target outcomes including one or more sexual intimacy outcomes (e.g., increase the frequency of sexual encounters).

In the same or different implementations, the template developing operation 304 may include an operation 557 for developing the template designed to facilitate the one or more end users to achieve the one or more target outcomes including one or more academic or intellectual outcomes as depicted in FIG. 5e. For instance, the template developing module 104 of the computing device 10 developing the template 16 designed to facilitate the one or more end users 4* to achieve the one or more target outcomes including one or more academic or intellectual outcomes (e.g., understanding particular concepts introduced in a book, accepted for enrollment at a particular University, and so forth).

In the same or different implementations, the template developing operation 304 may include an operation 558 for developing the template designed to facilitate the one or more end users to achieve the one or more target outcomes including one or more spiritual or religious outcomes as depicted in FIG. 5e. For instance, the template developing module 104 of the computing device 10 developing the template 16 designed to facilitate the one or more end users 4* to achieve the one or more target outcomes including one or more spiritual or religious outcomes (e.g., achieve spiritual harmony, acceptance to a particular church or religion, and so forth).

In the same or different implementations, the template developing operation 304 may include an operation 559 for developing the template designed to facilitate the one or more end users to achieve the one or more target outcomes including one or more user state outcomes as depicted in FIG. 5e. For instance, the template developing module 104 of the computing device 10 developing the template 16 designed to facilitate the one or more end users 4* to achieve the one or more target outcomes including one or more user state outcomes (e.g., achieve certain subjective user states such as being "happy" or "content," achieve certain social states such as being married, and so forth).

Figure 6:
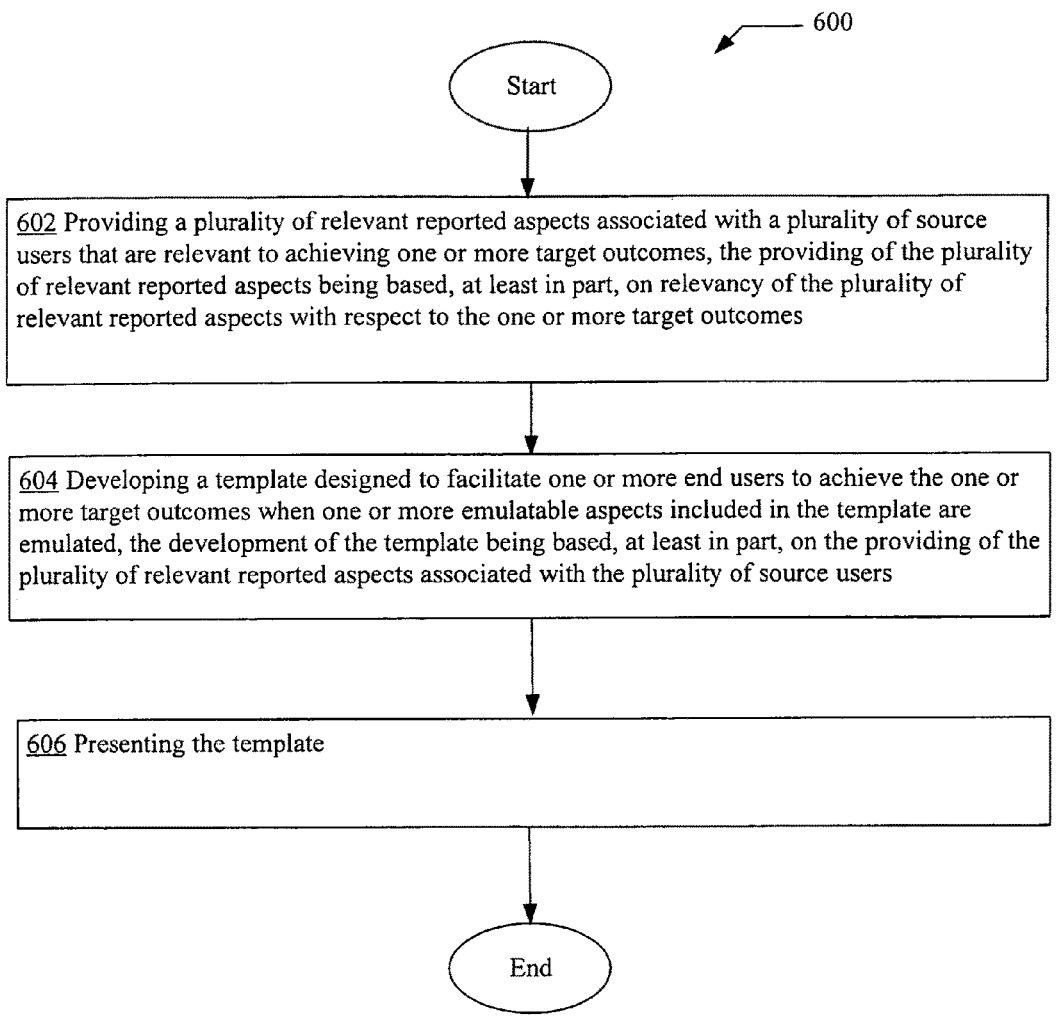
FIG. 6 is a high-level logic flowchart of another process.

Referring to FIG. 6 illustrating another operational flow 600 in accordance with various embodiments. Operational flow 600 includes certain operations that mirror the operations included in the operational flow 300 of FIG. 3. These operations include a relevant reported aspect providing operation 602 and a template developing operation 604 that corresponds to and mirror the relevant reported aspect providing operation 302 and the template developing operation 304, respectively, of FIG. 3.

In addition, operational flow 600 includes a template presenting operation 606 for presenting the template as depicted in FIG. 6. For instance, the template presenting module 106 of the computing device 10 presenting the template 16 resulting from the template developing operation 604.

Figure 7:
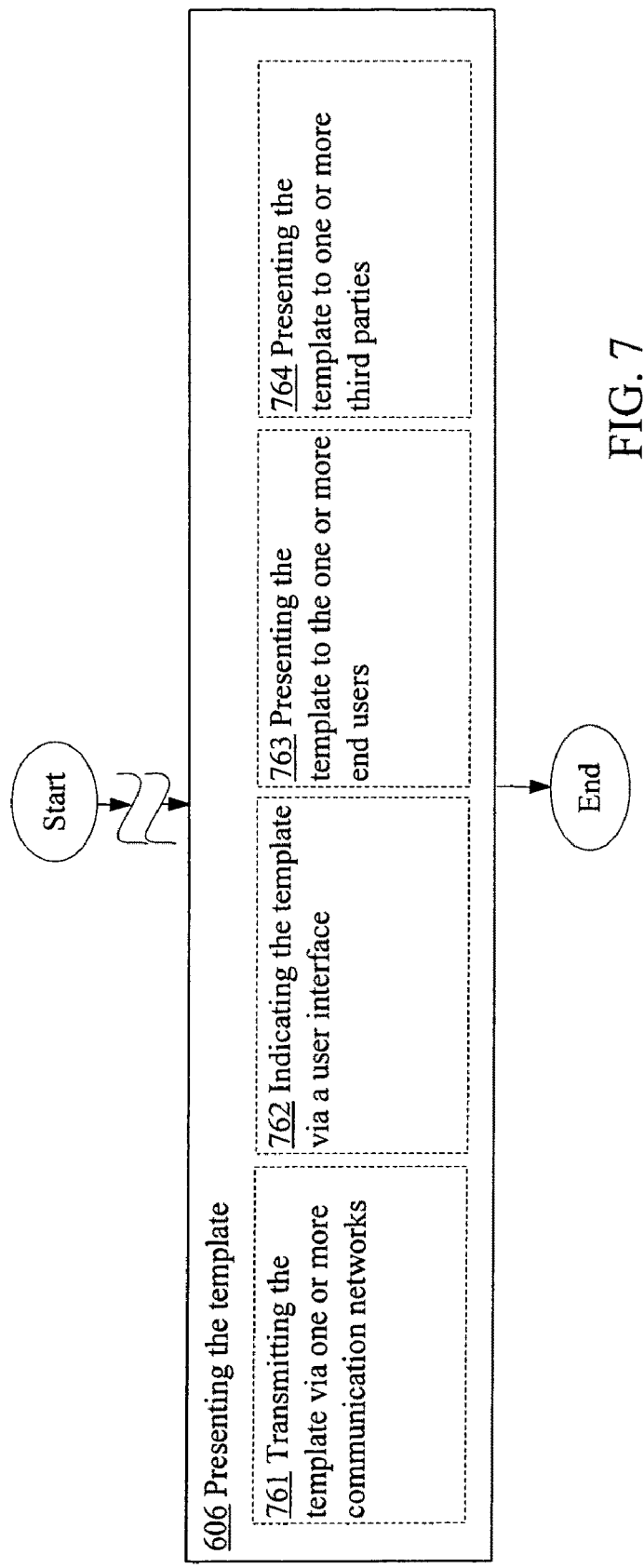
FIG. 7 is a high-level logic flowchart of a process depicting alternate implementations of the template presenting operation 606 of FIG. 6.

In some implementations, the template presenting operation 606 of FIG. 6 may include an operation 761 for transmitting the template via one or more communication networks as depicted in FIG. 7. For instance, the template transmitting module 150 (see FIG. 1b) of the computing device 10 transmitting the template 16 via one or more communication networks 50.

In the same or different implementations, the template presenting operation 606 may include an operation 762 for indicating the template via a user interface as depicted in FIG. 7. For instance, the template indicating module 152 of the computing device 10 indicating the template 16 via a user interface 120 (e.g., a display monitor, a touch screen, one or more speakers, and so forth).

In the same or different implementations, the template presenting operation 606 may include an operation 763 for presenting the template to the one or more end users as depicted in FIG. 7. For instance, the template presenting module 106 of the computing device 10 presenting the template 16 to the one or more end users 4*.

In the same or different implementations, the template presenting operation 606 may include an operation 764 for presenting the template to one or more third parties as depicted in FIG. 7. For instance, the template presenting module 106 of the computing device 10 presenting the template 16 to one or more third parties 6 (e.g., health or medical entities such as a doctor's office, a future end user 4*, and so forth).

Figure 8:
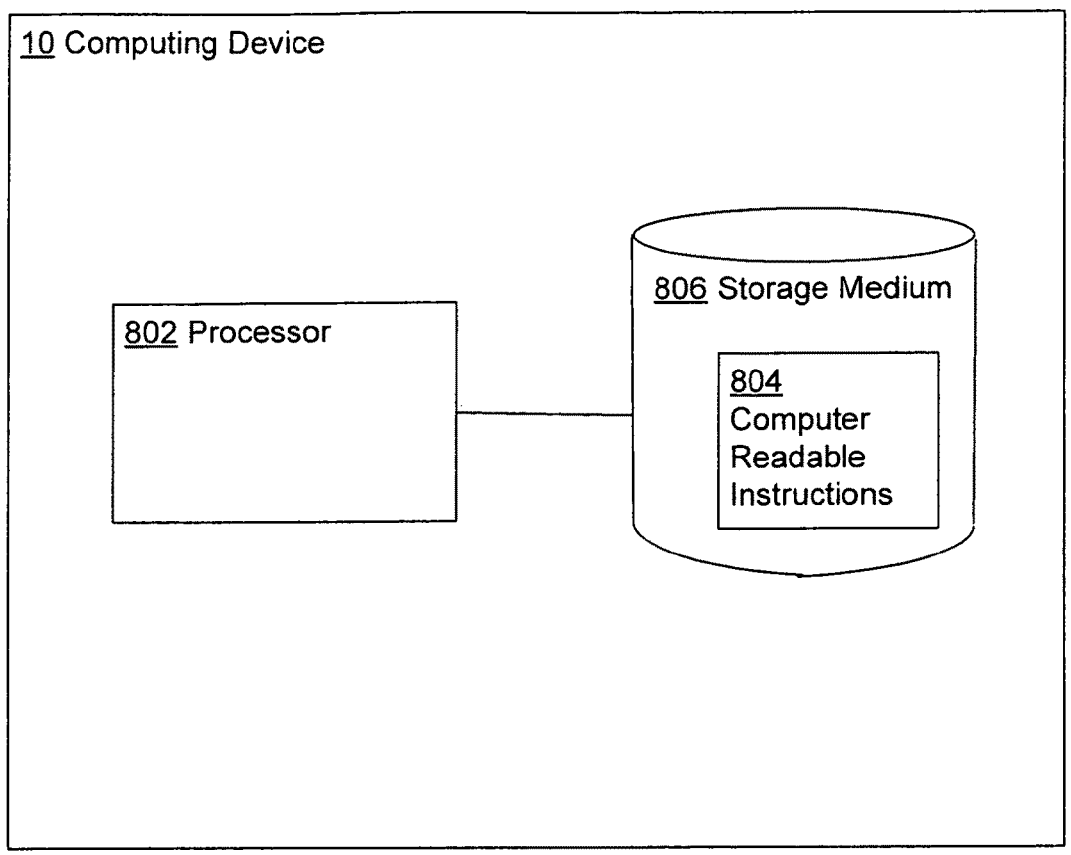
FIG. 8 is another high-level block diagram showing one implementation of the computing device 10 of FIG. 1b.

Turning now to FIG. 8, which is a high-level block diagram illustrating a particular implementation of the computing device 10 of FIG. 1b. As illustrated, the computing device 10 may include a processor 802 (e.g., microprocessor, controller, and so forth) coupled to a storage medium 806 (e.g., volatile or non-volatile memory). The storage medium 806 may store computer readable instructions 804 (e.g., computer program product). The processor 802, in various implementations, may execute the computer readable instructions 804 in order to execute one or more operations described above and as illustrated in FIGS. 3, 4a, 4b, 4c, 4d, 4e, 5a, 5b, 5c, 5d, 5e, 6, and 7.

For example, the processor 802 may execute the computer readable instructions 804 in order to provide a plurality of relevant reported aspects 14 associated with a plurality of source users 2* that are relevant to achieving one or more target outcomes, the providing of the plurality of relevant reported aspects 14 being based, at least in part, on relevancy of the plurality of relevant reported aspects 14 with respect to the one or more target outcomes; and/or to develop a template 16 designed to facilitate one or more end users 4* to achieve the one or more target outcomes when one or more emulatable aspects included in the template 16 are emulated, the development of the template 16 being based, at least in part, on the providing of the plurality of relevant reported aspects 14 associated with the plurality of source users 2* as illustrated by the operational flow 300 of FIG. 3.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system, comprising:
   a relevant reported aspect providing module configured to provide a plurality of relevant reported aspects associated with a plurality of source users that are relevant to achieving one or more target outcomes, the providing being based, at least in part, on relevancy of the plurality of relevant reported aspects with respect to the one or more target outcomes; and
   a template developing module configured to develop a template based, at least in part, on the providing of the plurality of relevant reported aspects associated with the plurality of source users, the template designed to facilitate one or more end users to achieve the one or more target outcomes when one or more emulatable aspects included in the template are emulated, wherein said template developing module comprises:
   an emulatable aspect including module configured to include into the template one or more emulatable aspects that were derived by an emulatable aspect deriving module based, at least in part, on the plurality of relevant reported aspects that are associated with the plurality of source users and that are relevant to achieving the one or more target outcomes, wherein said emulatable aspect including module comprises:
   an emulatable aspect deriving module configured to derive at least one emulatable aspect based, at least in part, on a plurality of relevant reported aspects that are each associated with different source users, the at least one emulatable aspect to be included into the template, wherein said emulatable aspect deriving module comprises:
   a plausible emulatable aspect determining module configured to determine whether at least one emulatable aspect to be included in the template is at least one plausible emulatable aspect that has been successfully emulated by one or more third parties who share at least one common trait with the one or more end users.

2. The system of claim 1, wherein said relevant reported aspect providing module comprises:
   a target outcome corresponding reported aspect identifying module configured to identify reported aspects that correspond to the one or more target outcomes.

3. The system of claim 2, wherein said relevant reported aspect providing module comprises:
   a source user identifying module configured to identify the source users based on the source users' association with the identified reported aspects that corresponds to the one or more target outcomes.

4. The system of claim 3, wherein said relevant reported aspect providing module comprises:
   an identified source user associated reported aspect providing module configured to provide reported aspects that are at least associated with the identified source users.

5. The system of claim 4, wherein said relevant reported aspect providing module comprises:
   a relevancy factor relevant reported aspect providing module configured to provide, from the reported aspects that are at least associated with the identified source users, reported aspects that are relevant with respect to one or more relevancy factors.

6. The system of claim 5, wherein said relevancy factor relevant reported aspect providing module comprises:
   a relevancy factor relevant reported aspect providing module configured to provide reported aspects that are at least associated with the identified source users and that belong to one or more aspect types that are of interest to the one or more end users.

7. The system of claim 5, wherein said relevancy factor relevant reported aspect providing module comprises:
   a relevancy factor relevant reported aspect providing module configured to provide reported aspects that are at least associated with the identified source users and that belong to one or more aspect types that have been indicated by at least one source user as being relevant to the achievement of the one or more target outcomes.

8. The system of claim 5, wherein said relevancy factor relevant reported aspect providing module comprises:
   a relevancy factor relevant reported aspect providing module configured to provide reported aspects that are at least associated with the identified source users and that belong to one or more aspect types that have been indicated by at least one third party source as being relevant to the achievement of the one or more target outcomes.

9. The system of claim 5, wherein said relevancy factor relevant reported aspect providing module comprises:
a relevancy factor relevant reported aspect providing module configured to provide reported aspects that are at least associated with the identified source users and that indicate aspects of the identified source users that occurred within one or more predefined time periods, respectively, from occurrences of the reported aspects that were identified as corresponding to the one or more target outcomes.

10. The system of claim 9, wherein said relevancy factor relevant reported aspect providing module comprises:
a relevancy factor relevant reported aspect providing module configured to provide reported aspects that are at least associated with the identified source users and that indicate aspects of the identified source users that occurred prior to and within one or more predefined time periods, respectively, from occurrences of the reported aspects that were identified as corresponding to the one or more target outcomes.

11. The system of claim 1, wherein said relevant reported aspect providing module comprises:
a relevant reported aspect providing module configured to provide one or more relevant reported aspects that were at least originally reported via one or more log entries.

12. The system of claim 11, wherein said relevant reported aspect providing module comprises:
a relevant reported aspect providing module configured to provide one or more relevant reported aspects that were at least originally reported via one or more social networking entries.

13. The system of claim 12, wherein said relevant reported aspect providing module comprises:
a relevant reported aspect providing module configured to provide one or more relevant reported aspects that were at least originally reported via one or more blog entries.

14. The system of claim 12, wherein said relevant reported aspect providing module comprises:
a relevant reported aspect providing module configured to provide one or more relevant reported aspects that were at least originally reported via one or more status reports.

15. The system of claim 11, wherein said relevant reported aspect providing module comprises:
a relevant reported aspect providing module configured to provide one or more relevant reported aspects that were at least originally reported via one or more journal entries.

16. The system of claim 11, wherein said relevant reported aspect providing module comprises:
a relevant reported aspect providing module configured to provide one or more relevant reported aspects that were at least originally reported by one or more of the source users.

17. The system of claim 11, wherein said relevant reported aspect providing module comprises:
a relevant reported aspect providing module configured to provide one or more relevant reported aspects that were at least originally reported by one or more third parties.

18. The system of claim 11, wherein said relevant reported aspect providing module comprises:
a relevant reported aspect providing module configured to provide one or more relevant reported aspects that were at least originally reported by one or more sensors.

19. The system of claim 1, wherein said relevant reported aspect providing module comprises:
a relevant reported aspect providing module configured to provide a first one or more reported aspects that are associated with a first source user and that are relevant to achieving at least one of the one or more target outcomes and providing a second one or more reported aspects that are associated with a second source user and that are relevant to achieving the at least one of the one or more target outcomes, the providing of the first one or more reported aspects and the second one or more reported aspects being based on the first one or more reported aspects' and the second one or more reported aspects' relevancy with respect to the at least one of the one or more target outcomes.

20. The system of claim 1, wherein said relevant reported aspect providing module comprises:
a relevant reported aspect providing module configured to provide a plurality of relevant reported aspects related to a plurality of behavior incidences associated with the plurality of source users.

21. The system of claim 1, wherein said relevant reported aspect providing module comprises:
a relevant reported aspect providing module configured to provide a plurality of relevant reported aspects related to a plurality of incidences of user beliefs associated with the plurality of source users.

22. The system of claim 1, wherein said relevant reported aspect providing module comprises:
a relevant reported aspect providing module configured to provide a plurality of relevant reported aspects related to a plurality of incidences of user states associated with the plurality of source users.

23. The system of claim 1, wherein said relevant reported aspect providing module comprises:
a relevant reported aspect providing module configured to provide a plurality of relevant reported aspects related to a plurality of incidences of user physical characteristics associated with the plurality of source users.

24. The system of claim 1, wherein said relevant reported aspect providing module comprises:
a relevant reported aspect providing module configured to provide a plurality of relevant reported aspects related to a plurality of incidences of user locations associated with the plurality of source users.

25. The system of claim 1, wherein said relevant reported aspect providing module comprises:
a relevant reported aspect providing module configured to provide a plurality of relevant reported aspects related to a plurality of incidences of external events associated with the plurality of source users.

26. The system of claim 1, wherein said emulatable aspect deriving module comprises:
an emulatable aspect deriving module configured to derive the at least one emulatable aspect based, at least in part, on a first relevant reported aspect that is associated with a first source user and a second relevant reported aspect that is associated with a second source user.

27. The system of claim 26, wherein said emulatable aspect deriving module comprises:
an emulatable aspect deriving module configured to derive a second emulatable aspect to be included in the template and based, at least in part, on a third relevant reported aspect that is associated with the first source user and a fourth relevant aspect that is associated with the second source user.

28. The system of claim 26, wherein said emulatable aspect deriving module comprises:

an emulatable aspect deriving module configured to derive a second emulatable aspect to be included into the template and based, at least in part, on a third relevant reported aspect that is associated with a third source user and a fourth relevant reported aspect that is associated with a fourth source user.

29. The system of claim 1, wherein said emulatable aspect deriving module comprises:
a commonly reported aspect determining module configured to determine a commonly reported aspect that is determined to be associated with two or more of the plurality of source users.

30. The system of claim 29, wherein said commonly reported aspect determining module comprises:
a commonly reported aspect determining module configured to determine a commonly reported aspect that is determined to be associated with a majority of the plurality of source users.

31. The system of claim 1, wherein said emulatable aspect deriving module comprises:
an emulatable aspect deriving module configured to derive at least one emulatable aspect that includes at least a portion that was derived based, at least in part, on deviations of the plurality of relevant reported aspects with respect to each other.

32. The system of claim 31, wherein said emulatable aspect deriving module comprises:
a mean value determining module configured to determine a mean value for the plurality of relevant reported aspects.

33. The system of claim 31, wherein said emulatable aspect deriving module comprises:
an average value determining module configured to determine an average value for the plurality of relevant reported aspects.

34. The system of claim 1, wherein said emulatable aspect deriving module comprises:
a compliant determining module configured to determine whether at least one emulatable aspect to be included into the template is compliant with one or more limitations associated with at least one of the one or more end users.

35. The system of claim 1, wherein said emulatable aspect deriving module comprises:
a plausible emulatable aspect determining module configured to determine whether at least one plausible emulatable aspect to be included in the template is at least one plausible emulatable aspect that has been successfully emulated by one or more third parties in order to achieve the one or more target outcomes.

36. The system of claim 1, wherein said template developing module comprises:
a template developing module configured to develop a template designed to facilitate the one or more end users to achieve one or more health or medical outcomes.

37. The system of claim 1, wherein said template developing module comprises:
a template developing module configured to develop a template designed to facilitate the one or more end users to achieve one or more athletic or gaming outcomes.

38. The system of claim 1, wherein said template developing module comprises:
a template developing module configured to develop a template designed to facilitate the one or more end users to achieve one or more occupational outcomes.

39. The system of claim 1, wherein said template developing module comprises:

a template developing module configured to develop a template designed to facilitate the one or more end users to achieve one or more social or leisure outcomes.

40. The system of claim 1, wherein said template developing module comprises:
a template developing module configured to develop a template designed to facilitate the one or more end users to achieve one or more academic or intellectual outcomes.

41. The system of claim 1, wherein said template developing module comprises:
a template developing module configured to develop a template designed to facilitate the one or more end users to achieve one or more spiritual or religious outcomes.

42. The system of claim 1, wherein said template developing module comprises:
a template developing module configured to develop a template designed to facilitate the one or more end users to achieve one or more user state outcomes.

43. The system of claim 1, further comprising:
a template presenting module configured to present the template.

44. A system, comprising:
circuitry for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and
circuitry for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users, wherein said circuitry for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users comprises:
circuitry for including into the template one or more emulatable aspects that were derived based, at least in part, on the plurality of relevant reported aspects that are associated with the plurality of source users and that are relevant to achieving the one or more target outcomes, wherein said circuitry for including into the template one or more emulatable aspects that were derived based, at least in part, on the plurality of relevant reported aspects that are associated with the plurality of source users and that are relevant to achieving the one or more target outcomes comprises:
circuitry for deriving at least one emulatable aspect based, at least in part, on a plurality of relevant reported aspects that are each associated with different source users, the at least one emulatable aspect to be included into the template, wherein said circuitry for deriving at least one emulatable aspect based, at least in part, on a plurality of relevant reported aspects that are each associated with different source users, the at least one emulatable aspect to be included into the template comprises:
circuitry for determining whether at least one emulatable aspect to be included in the template is at least one plausible emulatable aspect that has been successfully emulated by one or more third parties who share at least one common trait with the one or more end users.

45. An article of manufacture, comprising:
a non-transitory storage medium bearing:
one or more instructions for providing a plurality of relevant reported aspects associated with a plurality of source users that are relevant to achieving one or more target outcomes, the providing of the plurality of relevant reported aspects being based, at least in part, on relevancy of the plurality of relevant reported aspects with respect to the one or more target outcomes; and
one or more instructions for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users, wherein said one or more instructions for developing a template designed to facilitate one or more end users to achieve the one or more target outcomes when one or more emulatable aspects included in the template are emulated, the development of the template being based, at least in part, on the providing of the plurality of relevant reported aspects associated with the plurality of source users comprises:
one or more instructions for including into the template one or more emulatable aspects that were derived based, at least in part, on the plurality of relevant reported aspects that are associated with the plurality of source users and that are relevant to achieving the one or more target outcomes, wherein said one or more instructions for including into the template one or more emulatable aspects that were derived based, at least in part, on the plurality of relevant reported aspects that are associated with the plurality of source users and that are relevant to achieving the one or more target outcomes comprises:
one or more instructions for deriving at least one emulatable aspect based, at least in part, on a plurality of relevant reported aspects that are each associated with different source users, the at least one emulatable aspect to be included into the template, wherein said one or more instructions for deriving at least one emulatable aspect based, at least in part, on a plurality of relevant reported aspects that are each associated with different source users, the at least one emulatable aspect to be included into the template comprises:
one or more instructions for determining whether at least one emulatable aspect to be included in the template is at least one plausible emulatable aspect that has been successfully emulated by one or more third parties who share at least one common trait with the one or more end users.

\* \* \* \* \*